United States Patent
Rands et al.

(10) Patent No.: US 12,157,723 B2
(45) Date of Patent: *Dec. 3, 2024

(54) COMPOUNDS

(71) Applicant: CYBIN UK LTD, London (GB)

(72) Inventors: Peter Rands, London (GB); George Knight, London (GB); Richard Chubb, London (GB); Derek Londesbrough, London (GB); Tiffanie Benway, London (GB); Zelah Joel, London (GB)

(73) Assignee: CYBIN UK LTD, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/152,465

(22) Filed: Jan. 10, 2023

(65) Prior Publication Data
US 2023/0167056 A1 Jun. 1, 2023

Related U.S. Application Data

(60) Division of application No. 17/662,261, filed on May 6, 2022, now Pat. No. 11,578,039, which is a continuation of application No. PCT/EP2020/081502, filed on Nov. 9, 2020.

(30) Foreign Application Priority Data

Nov. 7, 2019 (GB) .................................. 1916210
Nov. 28, 2019 (GB) .................................. 1917320
Jun. 2, 2020 (GB) .................................. 2008303

(51) Int. Cl.
*C07D 209/16* (2006.01)
*C07D 209/20* (2006.01)

(52) U.S. Cl.
CPC ......... *C07D 209/16* (2013.01); *C07D 209/20* (2013.01); *C07B 2200/05* (2013.01)

(58) Field of Classification Search
CPC .............................. C07D 209/16; C07D 209/20
See application file for complete search history.

(56) References Cited

U.S. PATENT DOCUMENTS

| | | | |
|---|---|---|---|
| 4,336,378 A | 6/1982 | Brand et al. | |
| 8,268,856 B2 | 9/2012 | Hamann et al. | |
| 11,000,534 B1 | 5/2021 | Sippy | |
| 11,242,318 B2 | 2/2022 | Nivorozhkin et al. | |
| 11,406,619 B2 * | 8/2022 | Layzell ................ | A61K 9/0019 |
| 11,471,417 B2 | 10/2022 | Rands et al. | |
| 11,578,039 B2 | 2/2023 | Rands et al. | |
| 11,643,390 B2 | 5/2023 | Rands et al. | |
| 11,660,289 B2 | 5/2023 | Rands et al. | |
| 11,697,638 B2 * | 7/2023 | Rands ................... | C07D 209/16 |
| | | | 548/504 |
| 11,773,062 B2 | 10/2023 | Rands et al. | |
| 2002/0022667 A1 | 2/2002 | Pace et al. | |
| 2009/0076121 A1 | 3/2009 | Czarnik | |
| 2013/0129812 A1 | 5/2013 | Ozpolat et al. | |
| 2018/0221396 A1 | 8/2018 | Chadeayne | |
| 2020/0339519 A1 | 10/2020 | Kim et al. | |
| 2020/0390746 A1 | 12/2020 | Rands et al. | |
| 2021/0378969 A1 | 12/2021 | Rands et al. | |
| 2021/0395201 A1 | 12/2021 | Rands et al. | |
| 2021/0403426 A1 | 12/2021 | Rands et al. | |
| 2022/0062237 A1 | 3/2022 | Layzell et al. | |
| 2022/0062238 A1 | 3/2022 | Layzell et al. | |
| 2022/0081396 A1 | 3/2022 | Rands et al. | |
| 2022/0168275 A1 | 6/2022 | Rands et al. | |
| 2022/0202775 A1 | 6/2022 | Rands et al. | |

(Continued)

FOREIGN PATENT DOCUMENTS

GB    2585978 A    1/2021
GB    2586940 A    3/2021

(Continued)

OTHER PUBLICATIONS

Barker et al., "Metabolism of the Hallucinogen N,N-Dimethyltryptamine in Rat Brain Homogenates", Biochemical Pharmacology, vol. 29, pp. 1059-1057. 1980.
Rands et al., Unpublished U.S. Appl. No. 18/193,866, filed Mar. 31, 2023.
Rands et al., Unpublished U.S. Appl. No. 18/056,771, filed Nov. 18, 2022.
Rands et al., Unpublished U.S. Appl. No. 18/163,388, filed Feb. 2, 2023.
Reiff et al., "Psychedelics and Psychedelic-Assisted Psychotherapy", Am J. Psychiatry, 177:5, pp. 391-410. May 2020.

(Continued)

*Primary Examiner* — Rebecca L Anderson
(74) *Attorney, Agent, or Firm* — Heslin Rothenberg Farley & Mesiti P.C.

(57) ABSTRACT

The present invention relates to compounds of formula I, or pharmaceutically acceptable salts thereof, as well as compositions comprising such compounds. These compounds and compositions have uses in the treatment of psychiatric or neurological disorders. Compounds of formula I comprise at least one deuterium atom at the α-position and consequently have improved oral bioavailability relative to α-diprotic analogues.

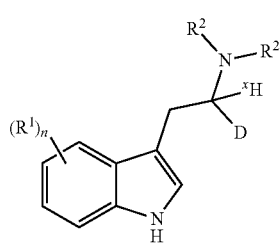

I

20 Claims, 2 Drawing Sheets

(56) References Cited

U.S. PATENT DOCUMENTS

| | | | |
|---|---|---|---|
| 2022/0281818 | A1 | 9/2022 | Rands et al. |
| 2022/0313660 | A1 | 10/2022 | Layzell et al. |
| 2023/0086574 | A1 | 3/2023 | Rands et al. |
| 2023/0149293 | A1 | 5/2023 | Rands et al. |
| 2023/0181530 | A1 | 6/2023 | Rands et al. |
| 2023/0250059 | A1 | 8/2023 | Rands et al. |
| 2024/0016782 | A1 | 1/2024 | Rands et al. |

FOREIGN PATENT DOCUMENTS

| | | | |
|---|---|---|---|
| GB | 2596884 | A | 1/2022 |
| WO | 02083144 | A1 | 10/2002 |
| WO | 2004085392 | A1 | 10/2004 |
| WO | 2008049116 | A2 | 4/2008 |
| WO | 2008071455 | A1 | 6/2008 |
| WO | 2009049030 | A1 | 4/2009 |
| WO | 2018195455 | A1 | 10/2018 |
| WO | 2019081764 | A1 | 5/2019 |
| WO | 2020169850 | A1 | 8/2020 |
| WO | 2020169851 | A1 | 8/2020 |
| WO | 2020176597 | A1 | 9/2020 |
| WO | 2020176599 | A1 | 9/2020 |
| WO | 2020245133 | A1 | 12/2020 |
| WO | 2021089872 | A1 | 5/2021 |
| WO | 2021089873 | A1 | 5/2021 |
| WO | 2021116503 | A2 | 6/2021 |
| WO | 2021155470 | A1 | 8/2021 |
| WO | 2021234608 | A1 | 11/2021 |
| WO | 2021244831 | A1 | 12/2021 |
| WO | 2022031566 | A1 | 2/2022 |
| WO | 2022043227 | A1 | 3/2022 |
| WO | 2022069690 | A2 | 4/2022 |
| WO | 2022117359 | A1 | 6/2022 |
| WO | 2022117640 | A1 | 6/2022 |

OTHER PUBLICATIONS

Atzrodt et al. Deuterium- and Tritium-Labelled Compounds: Applications in the Life Sciences, Angew. Chem. Int. Ed., vol. 57, pp. 1758-1784. 2018.

U.S. Appl. No. 18/252,949 to Rands et al. May 15, 2023.

Kazakevich et al., "HPLC For Pharmaceutical Scientists", Chapters 14 and 21, 71 pages. May 16, 2006.

Ambinter Screening Library, CAS Registry No. 1794811-18-9, Order No. Cat. Amb33838664 Mar. 26, 2020.

Aurora Building Blocks 2, CAS Registry No. 1435934-64-7, Order No. Cat A17.921.638. Feb. 27, 2020.

Barker, et al., "Comparison of the Brain Levels of N N-Dimethyltryptamine and a,a, B,B-Tetradeutero N, N-Dimethyltryptamine Following Intraperitoneal Injection", Biochemical Pharmacology, vol. 31, No. 15, pp. 2513-2516 Jan. 20, 1982.

Barker, Steven A., "N, N-Dimethyltryptamine (DMT), an Endogenous Hallucinogen: Past, Present, and Future Research to Determine Its Role and Function", Frontiers in Neuroscience, vol. 12, Article 536, pp. 1-17 Aug. 6, 2018.

Beaton, et al., "A Comparison of the Behavioral Effects of Proteo- and Deutero-N, N-Dimethyltryptamine", Pharmacology, Biochemistry & Behavior, vol. 16, pp. 811-814 Sep. 8, 1982.

Brandt, et al., "Microwave-Accelerated Synthesis of Psychoactive Deuterated N, N-Dialkylated-[a, a, ?, ?- d4]- Tryptamines", Journal of Labelled Compounds and Radiopharmaceuticals, vol. 51, No. 14, pp. 423-429 Nov. 1, 2008.

Brito-Da-Costa et al. "Toxicokinetics and Toxicodynamics of Ayahuasca Alkaloids N,N-Dimethyltryptamine (DMT), Harmine, Harmaline and Tetrahydroharmine: Clinical and Forensic Impact", Pharmaceuticals, vol. 13, No. 334, 36 pages. Oct. 23, 2020.

Cameron, et el., "Effects of N,N-Dimethyltryptamine on Rat Behaviors Relevant to Anxiety and Depression", ACS Chemical Neuroscience, vol. 9, No. 7, pp. 1582-1590 2018.

Celik, et al., "Binding of Serotonin to the Human Serotonin Transporter. Molecular Modeling and Experimental Validation" Journal of the American Chemical Society, vol. 130, No. 12, pp. 3853-3865 Mar. 2008.

Celik, et al., "Supplementary Information to Binding of Serotonin to the Human Serotonin Transporter. Molecular Modeling and Experimental Validation", Journal of the American Chemical Society, 14 pages Mar. 2008.

Chemieliva Pharmaceutical Product, Cas Registry No. 1794756-39-0, "Supplementary Disclosures", Chemieliva Pharmaceutical Product List, Order No. Cat. CC0034145 Jan. 28, 2021.

Chemieliva Pharmaceutical Product, Cas Registry No. 1794811-18-9, "Supplementary Disclosures", Chemieliva Pharmaceutical Product List, Order No. Cat. CC0034141 Jan. 28, 2021.

Davis et al., "5-methoxy-N, N-dimethyltryptamine (5-MeO-DMT) used in a naturalistic group setting is associated with unintended improvements in depression and anxiety", The American Journal of Drug and Alcohol Abuse, 10 pages. Mar. 1, 2019.

Dragulska et al., "Isotope Effects in the Enzymatic Oxidation of Tryptamine to 3-indolyl-acetaldehyde", Isotopes in Environmental and Health Studies, vol. 50, No. 2, pp. 269-276. 2014.

Dunlap et al., "Identification of Psychoplastogenic N,N-Dimethylaminoisotryptamine (isoDMT) Analogues through Structure—Activity Relationship Studies", Journal of Medicinal Chemistry, vol. 63, pp. 1142-1155 2020.

Dyck, et al., "Effect of Deuterium Substitution on the Disposition of Intraperitoneal Tryptamine", Biochemical Pharmacology, vol. 35, No. 17, pp. 2893-2896 1986.

Gaujac, et al., Investigations into the polymorphic properties of N, N-dimethyltryptamine by X-ray diffraction and differential scanning calorimetry, Microchemical Journal, vol. 110, pp. 146-157 2013.

Ghosal, et al., "Indole Bases of Desmodium Gyrans", Phytochemistry (Elsevier), vol. 11, No. 5, pp. 1863-1864 1972.

Grina, et al., "Old and New Alkaloids From Zanthoxylum Arborescens", Journal of Organic Chemistry, vol. 47, No. 13, pp. 2648-2651 1982.

Halberstadt, et al., "Behavorial effects of α,α,ß,ß-tetradeutero-5-MeO-DMT in rats: comparison with 5-MeO-DMT administered in combination with a monoamine oxidase inhibitor", Psychopharmacology, vol. 221, pp. 709-718. Jan. 6, 2012.

Ibrahim, et al., "Marine inspired 2-(5-Halo-1 H-indol-3-yl)-N, N-dimethylethanamines as Modulators of Serotonin Receptors: An Example Illustrating the Power of Bromine as Part of the Uniquely Marine Chemical Space", Marine drugs, vol. 15, No. (8), pp. 248/1-248/14 2017.

Kargbo "5-MeO-DMT: Potential Use of Psychedelic-Induced Experiences in the Treatment of Psychological Disorders", ACS Med. Chem. Lett. vol. 12, pp. 1646-1648. 2021.

McIlhenny, et al., "Direct Analysis of Psychoactive Tryptamine and Harmala Alkaloids in the Amazonian Botanical Medicine Ayahuasca by Liquid Chromatography-electrospray Ionization-tandem Mass Spectrometry", Journal of Chromatography A, vol. 1216, No. 51, 9 pages 2009.

Morris, et al., "Indolealkylamine Metabolism: Synthesis of Deuterated Indolealkylamines as Metabolic Probes", Journal of Labelled Compounds and Radiopharmaceuticals, John Wiley & Sons Ltd., vol. 33, No. 6, pp. 455-465 1993.

MuseChem Product List, CAS Registry No. 1794756-39-0, Order No. Cat. R055190. Apr. 21, 2020.

Pires et al., "Gas Chromatographic Analysis of Dimethyltryptamine and ß-Carboline Alkaloids in Ayahuasca, an Amazonian Psychoactive Plant Beverage", Phytochemical Analysis, vol. 20, pp. 149-153. Jan. 12, 2009.

Queiroz, et al., "Chemical Composition of the Bark of Tetrapterys Mucronata and Identification of Acetylcholinesterase Inhibitory Constituents", Journal of Natural Products, vol. 77, No. 3, 2014, pp. 650-656 2014.

Rands et al., Unpublished U.S. Appl. No. 17/469,063, filed Sep. 8, 2021.

Rands et al., Unpublished U.S. Appl. No. 17/574,424, filed Jan. 12, 2022.

(56) References Cited

OTHER PUBLICATIONS

Riga, et al., The serotonin hallucinogen 5-MeO-DMT alters cortico-thalamic activity in freely moving mice: Regionally-selective incolovement of 5-HT1A and 5-HT2A receptors, Neuropharmacology, vol. 142, pp. 219-230 2017.

Sard, et al., "SAR of psilocybin analogs: Discovery of a selective 5-HT2c agonist", Bioorganic & Medicinal Chemistry Letters 15, vol. 15, No. 20, pp. 4555-4559 2005.

Servillo, et al., "Citrus Genus Plants Contain N-Methylated Tryptamine Derivatives and Their 5-Hydroxylated Forms", Journal of Agricultural and Food Chemistry, vol. 61, No. 21, pp. 5156-5162 2013.

Sherwood et al., "Synthesis and Characterization of 5-MeO-DMT Succinate for Clinical Use", ACS Omega, vol. 5, pp. 32067-32075. 2020.

Silveira et al., "Stability Evaluation of DMT and Harmala Alkaloids in Ayahuasca Tea Samples", Molecules, vol. 25, 11 pages. 2020.

Strassman et al., "Dose-Response Study of N, N-Dimethyltryptamine in Humans: II. Subjective Effects and Preliminary Results of a New Rating Scale", Archives of General Psychiatry, Chicago, IL, vol. 51(2), pp. 98-108 Feb. 1994.

Tearavarich et al. "Microwave-Accelerated Preparation and Analytical Characterization of 5-ethoxy-N, N-dialkyl-[α, α,ß,ß-H4]- and [α,α,ß,ß-D4]-tryptamines", Drug Testing and Analysis, vol. 3, No. 9, pp. 597-608 Dec. 2010.

Timmins, Expert Opin Ther Pat., 24(10), pp. 1067-1075. Oct. 2014.

Usach et al., "Subcutaneous Injection of Drugs: Literature Review of Factors Influencing Pain Sensation at the Injection Site", Adv. Ther., vol. 36, pp. 2986-2996. Only Cite in 006A Oct. 5, 2019.

Walker, et al., "Gas Chromatographic-Mass Spectrometric Isotope Dilution Assay for N, N-Dimethyltryptamine in Human Plasma", Biochemical Medicine, vol. 8, pp. 105-113 1973.

Yu et al., "Stereospecific Deuterium Substitution at the a-Carbon Position of Dopamine and Its Effect on Oxidative Deamination Catalyzed by Mao-A and Mao-B From Different Tissues", Biochemical Pharmacology, vol. 35, No. 6, pp. 1027-1036. 1986.

Roseman et al., "Quality of Acute Psychedelic Experience Predicts Therapeutic Efficacy of Psilocybin for Treatment-Resistant Depression", Frontiers in Pharmacology, vol. 8, Article 974, 10 pages. Jan. 2018.

Rands et al., Unpublished U.S. Appl. No. 18/602,171, filed Mar. 12, 2024.

Rands et al., Unpublished U.S. Appl. No. 18/711,130, filed May 17, 2024.

Rands et al. Unpublished U.S. Appl. No. 18/619,547, filed Mar. 28, 2024.

Strassman et al., "Differential Tolerance to Biological and Subjective Effects of Four Closely Spaced Doses of N,N-Dimethyltryptamine in Humans", Biol. Psychiatry, vol. 39, pp. 784-795. 1996.

Timmermann et al., "Neural Correlates of the DMT Experience Assessed with Multivariate EEG", Scientific Reports, Nature Research, vol. 9, No. 16324, 13 pages. 2019.

* cited by examiner

COMPOUNDS

CROSS REFERENCE TO RELATED APPLICATIONS

This application is a divisional application of U.S. patent application Ser. No. 17/662,261, filed May 6, 2022, which is a continuation of International Application PCT/EP2020/081502, filed Nov. 9, 2020, and published as WO2021089872A1 on May 14, 2021. PCT/EP2020/081502 claims priority from Great Britain application numbers 1916210.6, filed Nov. 7, 2019, 1917320.2, filed Nov. 28, 2019, and 2008303.6 filed Jun. 2, 2020. The entire contents of each of these prior applications are hereby incorporated herein by reference.

FIELD OF THE INVENTION

The present invention relates to compounds of formula I, or pharmaceutically acceptable salts thereof, as well as compositions comprising such compounds. These compounds and compositions have uses in the treatment of psychiatric or neurological disorders. Compounds of formula I comprise at least one deuterium atom at the α-position and consequently have improved oral bioavailability relative to α-diprotic analogues.

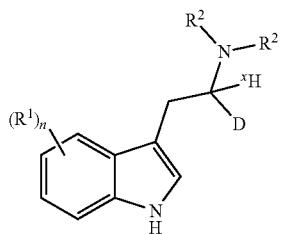

BACKGROUND OF THE INVENTION

N,N-dimethyltryptamine (DMT) is an indole alkaloid found endogenously in many species of plants and animals, including humans (S. A. Barker, E. H. McIlhenny and R. Strassman, *Drug Test. Anal.*, 2012, 4, 617-635). It has a long history of use within Mesoamerican and South American cultures, with archaeological evidence for its use via smoking dating back to c.2130 BC (C. M. Torres, *Ann. Mus. civ. Rovereto, Sez. Arch., St., Sc. nat.*, 1995, 11, 291-326). DMT is the psychedelic component of the Amazonian concoction ayahuasca, which has been used in ceremonious practices of indigenous people for centuries.

DMT was first synthesized in 1931 by chemist Richard Manske and then used in research studies during the 1950s by Dr. Stephen Szara, until the illegalisation of psychedelics occurred in the 1960s and put a halt to this line of research. In 1994, Dr. Rick Strassman successfully reinitiated research into DMT, and five studies have since been conducted in humans. An additional study is currently being undertaken at Imperial College London.

DMT has been shown to be safely administered in humans from a low dose of 0.05 mg/kg to a high dose of 0.4 mg/kg. Of the 5 studies conducted since 1994, 2 used single-bolus injections, one used repeat-bolus dosing and two used prolonged infusions (over 90 and 20 minutes). DMT was found to be well-tolerated, with only a small number of mild to moderate adverse effects observed, with most being categorised as either a negative psychological effect or a hypertensive response.

DMT is a non-selective serotonin receptor agonist with high affinity for the serotonin 5HT2A receptor, and structurally classed as a tryptamine. Recent studies have shown significant therapeutic effects of psilocybin, another tryptamine structurally related to the endogenous neurotransmitter serotonin. Efficacy of psilocybin has been shown in depression (R. L. Carhart-Harris et al., *Psychopharmacology*, 2018, 235, 399-408; R. L. Carhart-Harris et al., *Lancet Psychiatry*, 2016, 3, 7, 619-627), end of life anxiety (R. R. Griffiths et al., *J. Psychopharmacol.*, 2016, 30, 12, 1181-1197) and addiction (M. W. Johnson, A. Garcia-Romeu and R. R. Griffiths, *Am. J. Drug Alcohol Abuse*, 2017, 43, 1, 55-60), and is currently being investigated for several other mental health disorders that are rooted in psychologically destructive patterns of thought processing (Anorexia Nervosa: NCT #NCT04052568). Evidence produced by the lab of Dr. Carhart-Harris has found that the mechanisms of action of psilocybin share many commonalities with those of DMT.

Through the use of magnetoencephalography (MEG), electroencephalography (EEG) and functional magnetic resonance imaging (fMRI), the Carhart-Harris group has demonstrated that the psychedelic state induced by psilocybin (S. D. Muthukumaraswamy et al., *J. Neurosci.*, 2013, 33, 38, 15171-15183; M. M. Schartner et al., *Sci. Rep.*, 2017, 7, 46421), LSD (R. L. Carhart-Harris et al., 2016, 113, 17, 4853-4858; Schartner et al., 2017 (supra)) and DMT (C. Timmermann et al., *Sci. Rep.*, 2019, 9, 16324) is associated with a decrease in oscillatory power across a range of frequency bands, and increasing spontaneous signal diversity and global integration of brain networks. This work is compiled into the entropic brain hypothesis (R. L. Carhart-Harris, *Neuropharmacology*, 2018, 142, 167-178; R. L. Carhart-Harris et al., *Front. Hum. Neurosci.*, 2014, 8, 20, 1-22) and may explain the antidepressant effects of psilocybin recently reported by the group (R. L. Carhart-Harris et al., 2018 (supra); R. L. Carhart-Harris et al., 2016 (supra)).

An integral feature of the entropic brain hypothesis involves a part of the brain called the default mode network (DMN), which has been described as the conductor of global brain function (R. L. Carhart-Harris et al., 2014 (supra)). The DMN is engaged during higher-level, metacognitive operations such as thinking about oneself or others (P. Qin and G. Northoff, *Neuroimage*, 2011, 57, 3, 1221-1233; R. N. Spreng and C. L. Grady, *J. Cogn. Neurosci.*, 2010, 22, 6, 1112-1123), remembering the past, and thinking about the future (R. L. Buckner and D. C. Carroll, *Trends Cogn. Sci.*, 2007, 11, 2, 49-57).

Brain imaging work has suggested that increased DMN integrity may be a marker of depressed mood and specifically, depressive rumination (M. G. Berman et al., *Soc. Cogn. Effect.*, 2011, 6, 5, 548-555; J. P. Hamilton at al., *Biol. Psychiatry*, 2015, 78, 4, 224-230). Under psilocybin (R. L. Carhart-Harris et al., *PNAS*, 2012, 109, 6, 2138-2143), LSD (R. L. Carhart-Harris et al., 2016 (supra)), ayahuasca (F. Palhano-Fontes et al., *PLOS One*, 2015, 10, 2: e0118143) and DMT, decreased DMN functional integrity has been observed acutely, followed by an increase in its integrity post-acutely, as shown with psilocybin (R. L. Carhart-Harris et al., 2017 (supra)). The DMN integrity change correlates with improvements in mood for depressed patients (ibid.). The decrease and then increase in DMN integrity observed is consistent with the 'reset' mechanism hypothesis in which acute modular disintegration in the DMN enables a subsequent re-integration that then allows for normal functioning (ibid.).

The antidepressant effect consistent with the reset mechanism has been supported in multiple trials with psilocybin, as well as in preliminary trials with ayahuasca. In a pilot study by F. L. Osorio et al., *Braz. J. Pschiatry*, 2015, 31, 1, 13-20) six volunteers with recurrent MDD were administered a single-dose of ayahuasca, which produced rapid antidepressant and anxiolytic effects that were maintained for up to 21 days. These results were later confirmed in a larger sample by R. F. Sanches et al., *J. Clin. Psychopharmacol.*, 2016, 36, 1, 77-81. More recently, the antidepressant effects of ayahuasca have been tested in a randomised placebo-controlled trial of 29 patients with TRD (F. Palhano-Fontes et al., 2019, 49, 4, 655-663). Ayahuasca was again found to exert rapid antidepressant effects that were maintained up to day 7.

Further to the evidence observed with brain activity, the quality of the psychedelic experience felt by the individual also links to therapeutic outcome. Quality refers to the profundity of the psychological experience, often described as 'mystical' or 'spiritual', and is measured using questionnaires such as the Mystical Experience Questionnaire (MEQ) or the Altered States of Consciousness (ASC) questionnaire. Numerous studies have now shown the intensity of feelings of interconnectedness and unity, transcendence of time and space or sense of wonder, among others, are predictive of longer-term therapeutic outcome with psilocybin across a range of indications (M. P. Bogenschutz et al., *J. Psychopharmacol.*, 2015, 29, 3, 289-299; R. R. Griffiths et al., 2016 (supra); L. Roseman, D. J. Nutt and R. L. Carhart-Harris, *Front. Pharmacol.*, 2018, 8, 974). The DMT experience scores comparably to psilocybin on all such scales (C. Timmermann et al., *Front. Psychol.*, 2018, 9, 1424), further supporting its potential to have therapeutic benefit.

Data gathered from the imaging studies conducted with DMT provide strong evidence that it shares a mechanism of action with psilocybin, enabling a 'reset' to occur in the DMN that may facilitate therapeutic benefit. This is supported by the antidepressant effects observed in trials with ayahuasca, given DMT is the main component of the brew that induces the psychedelic state.

Additional preliminary evidence from the Carhart-Harris lab has shown a decrease in scores for neuroticism in the ongoing trial participants administered DMT. The trait neuroticism may play a critical role in the development of depressive disorders, as symptoms of depression have been shown to be associated with higher scores for neuroticism (H. Sauer et al., *J. Affect. Disord.*, 1997, 42, 2-3, 169-177). A key mediator between this personality trait and depressive disorder has been shown to be rumination, which, as stated previously, can be the manifestation of a too-rigid DMN. DMT may therefore provide a means by which to lower neuroticism and stop or prevent the onset or continuance of depressive rumination as part of a therapeutic benefit.

In view of the above, there is overwhelming evidence that clinical grade tryptamines, and especially DMT, should be investigated in large-scale clinical trials for a number of mental health conditions. However, there are currently no Good Manufacturing Practice (GMP) providers of DMT or any other tryptamine-derived psychedelic, aside from psilocybin.

Tryptamines are generally synthesised using methods adapted from Alexander Shulgin's pioneering publication TiHKAL: The Continuation (Berkeley, CA, Transform Press, 1997). This discloses several alternative methods for synthesising DMT; the three step route starting from indole using (1) oxalyl chloride, (2) dimethylamine and (3) lithium aluminium hydride has been widely adopted (see top synthetic route depicted in Scheme 1), and analogous routes have been used to scale psilocybin under GMP controls (see, for example, WO 2019/073379 A1). Oxalyl chloride is very toxic and corrosive. It is severely irritating to eyes, skin, and the respiratory tract and reacts violently with water making it difficult to handle at scale.

The synthesis of DMT from auxin (a plant hormone and natural product) has been reported by P. E. Morris and C. Chiao in *J. Lab. Comp. Radiopharm.*, 1993, 33, 6, 455-465 (see bottom synthetic route depicted in Scheme 1). Nevertheless, the oxalyl chloride route remains popular due to its high yield with respect to other known routes. Consequently, there is a need in the art for an alternative method for the synthesis of DMT and DMT-type compounds of formula I, which avoids the use of problematic oxalyl chloride whilst producing high-purity compounds of formula I without sacrificing yield.

5-methoxy-N,N-dimethyltryptamine (5-MeO-DMT) is a short-acting psychoactive indolealkylamine found endogenously in the bufotoxin venom of the Colorado River toad (T. Lyttle, D. Goldstein and J. Gartz, *J. Psychoact. Drugs*, 1996, 28, 3, 267-290; A. T. Weil and W. Davis, *J. Ethnopharmacol.*, 1994, 41, 1-2, 1-8), and in a variety of plant species including virola resin, peregrina seeds, and dictyoloma incanescens (C. M. Torres and D. B. Repke, *Anadenanthera: Visionary Plant of Ancient South America*, 2006, The Haworth Herbal Press, Oxford). 5-MeO-DMT is reported to have been used by indigenous cultures of the pre-Columbian Americas (T. Weil and W. Davis, 1994 (supra)), and was first synthetically prepared in 1936 (T. Hoshino and K. Shimodaira, *Bull. Chem. Soc. Jpn.*, 1936, 11, 3, 221-224).

As a structural analogue of serotonin, 5-MeO-DMT has affinity for the 5HT1A and 5HT2A receptor pathways, with particularly high affinity for 5HT1A, and also activates 5HT2A, 5HT3A, 5HT5, 5HT6 and 5HT7 receptors (A. L. Halberstadt and D. E. Nichols, *Handbook of Behavioral Neuroscience*, 2010, 21, 621-636; M. C. McBride, *J. Psychoactive Drugs*, 2000, 32, 3, 321-331). To a lesser degree, 5-MeO-DMT also activates the D1, D3, and alpha-2 receptors (T. S. Ray, *PLOS One*, 2010, 5, 2, e9019), and is aligand for σ1 receptors (A. Szabo et al., *PLOS One*, 2014, 9, 8, e106533).

5-MeO-DMT is an endogenous tryptamine found in human blood, urine, and spinal fluid (S. A. Barker, E. H. McIlhenny and R. Strassman, *Drug Test. Anal.*, 2012, 4, 7-8, 617-635; F. Benington, R. D. Morin and L. C. Clark, *J. Med. Sci.*, 1965, 2, 397-403; F. Franzen, and H. Gross, *Nature*, 206, 1052; R. B. Guchhait., *J. Neurochem.*, 1976, 26, 1, 187-190), and has been shown to exhibit protective and therapeutically relevant effects. Studies by V. Dakic et al. in *Sci. Rep.*, 2017, 7, 12863, and A. Szabo et al. in *PLOS One*, 2014, 9, 8, e106533, have shown 5-MeO-DMT to be neuroprotective, anti-inflammatory, and a modulator of both immune responses and morphogenesis of human brain cells. Anti-depressant properties have been shown in rodents administered 5-MeO-DMT in the form of increases in the prefrontal cortex theta band (M. S. Riga et al., *Neuropharmacology*, 2017, 113, A, 148-155), and changes in the activity of this area have been attributed to the efficacy of another psychedelic tryptamine, psilocybin, for treatment-resistant depression (R. L. Carhart-Harris et al, 2012 (supra)).

5-MeO-DMT is not orally bioavailable without coadministration alongside amonoamine oxidase inhibitor. However, inhaled 5-MeO-DMT reportedly produces potent visionary and auditory changes and alterations in time perception (J. Ott, *J. Psychoactive Drugs,* 2001, 33, 4, 403-407; Shulgin and Shulgin, 1997 (supra)), and is also rapidly metabolized, with a half-life of 12-19 min (H-W. Shen et al., *Curr. Drug. Metab.,* 2010, 11, 8, 659-666). Reports from experienced users suggest that inhalation of vaporized 5-MeO-DMT produces experiences that range from spiritual ecstasy and enlightenment, to feelings of near-death anxiety and panic (https-J/www.erowid.org/Aibrary/books_online/tihkal/tihkal38.shtml, 2018).

In an EEG study in humans, vaporized synthetic 5-MeO-DMT (2-5 mg) has been shown to produce a temporary reversible reconfiguration of brain network dynamics, which were found in the form of Alpha activity suppression, a shift from Alpha to Theta activity, increased gamma power, and induced hypercoherence in all bands. Subjects reported feelings of peace, calm, and clarity during the resolution phase (J. Acosta-Urquidi, *Cosmos and History: The Journal of Natural and Social Philosophy,* 2015, 11, 2, 115-129).

In an epidemiological study of over 500 individuals who have ingested 5-MeO-DMT in different forms in an uncontrolled setting, a high number of users reported therapeutic effects attributed to its use (A. K. Davis et al., *J. Psychopharmacol.,* 2018, 32, 7, 779-792). Participants described as having psychiatric diagnoses indicated that their symptoms improved following 5-MeO-DMT use, including post-traumatic stress disorder (79%), depression (77%), and anxiety (69%). These responders reported infrequent use (<once/year), and not more than four times in their lifetime. Additionally, 5-MeO-DMT reportedly demonstrated a safe profile, as evidenced by the low intensity of challenging experiences (e.g., fear, anxiety) and low addiction liability (i.e., very low rates of craving, or legal, medical, psychiatric treatment associated with consumption).

5-MeO-DMT has also exhibited the potential to treat substance abuse disorders. In a proteomics study, 5-MeO-DMT revealed anti-addictive properties due to its ability to downregulate metabotropic glutamate receptor 5 (V. Dakic et al., *Sci. Rep.,* 2017, 7, 12863), which is implicated in the rewarding effects of alcohol (M. K. Bird et al., *Int. J. Neuropharmacol.,* 2008, 11, 6, 765-774), cocaine (C. Chiamulera et al., *Nat. Neurosci.,* 2001, 4, 873-874), and nicotine withdrawal (A. K. Stoker, B. Olivier and A. Markou, *Psychopharmacology,* 2012, 221, 317-327). The primary mechanism of therapeutic action is its agonism of the 5HT1A and 5HT2A receptors, along with other classic psychedelics with similar serotonergic effects (e.g., LSD, psilocybin) that consistently demonstrate therapeutic potential in treating alcohol use disorders (F. S. Abuzzahab and B. J. Anderson, *Int. Pharmacopsychiatry,* 1971, 6, 223-235; T. S. Krebs and P-O. Johansen, *J. Psychopharmacol.,* 2012, 26, 7, 994-1002; E. M. Nielson et al., *Front. Pharmacol.,* 2018, 9, 132).

DMT, in the form of the brew ayahuasca, has shown a reduction in addictive behaviors in an animal model of alcohol dependence by inhibiting behavioral sensitization to alcohol (E. G. Cata-Preta et al., *Front. Pharmacol.,* 2018, 9, 561) which has been theorized to be due to the serotonergic properties of this tryptamine (Shen et al., 2010 (supra)). In the aforementioned epidemiological investigation of 5-MeO-DMT users, individuals with alcoholism or hazardous drinking (66%, n=75 out of 113) reported improvements in their conditions following 5-MeO-DMT use, suggesting initial evidence of potential as a therapeutic agent in alcohol use disorders.

A powerful predictive measure of therapeutic efficacy across treatment studies of different mental health disorders in humans is the occurrence of mystical-type experiences (M. P. Bogenschutz and M. W. Johnson, *Prog. Neuropsychopharmacol. Biol. Psychiatry,* 2016, 64, 4, 250-258; B. T. H. de Veen et al., *Expert Rev. Neurother.,* 2017, 17, 2, 203-212; A. Loizaga-Velder and R. Verres, *J. Psychoact. Drugs,* 2014, 46, 1, 63-72; Roseman et al., 2018 (supra)). In particular, studies on psilocybin-assisted treatment for alcohol dependence have found that the intensity of mystical experience is consistently identified as a key predictor of outcomes (M. P. Bogenschutz et al., 2015 (supra); M. P. Bogenschutz and M. W. Johnson, 2016 (supra); B. T. H. de Veen et al., 2017 (supra)). Given 5-MeO-DMT has been shown to reliably produce mystical-type experiences (Davis et al., 2018 (supra)) of similar or greater intensity than psilocybin (J. Barsuglia et al., *Front. Psychol.,* 2018, 9, 2459), it follows that 5-MeO-DMT is likely to possess similar or potentially greater efficacy in treating substance use disorders than psilocybin. This extends to other disorders that psilocybin has demonstrated efficacy, including depression (R. L. Carhart-Harris et al., 2018 (supra); R. L. Carhart-Harris, et al., 2016 (supra)), and end of life anxiety (R. R. Griffiths et al., 2016 (supra)), and possibly other disorders that are rooted in psychologically destructive patterns of thought processing (Anorexia Nervosa: NCT #NCT04052568).

DMT and its substituted analogues, such as 5-MeO-DMT, are inactivated through a deamination pathway mediated by monoamine oxidases (MAO). MAOs are found in most cell types of the body. Consequently, DMT and its substituted analogues, such as 5-MeO-DMT are often administered with MAO inhibitors (MAOIs) to prevent inactivation of the compounds before they have reached their target site in the body, allowing for a prolonged and increased exposure to the compound. As described above, 5-MeO-DMT is not orally bioavailable without co-administration with an MAOI. However, MAOIs can cause high blood pressure when taken with certain foods or medications, thus the use of MAOIs by a patient typically requires the patient to restrict their diet and avoiding some other medications.

In light of the therapeutic potential of substituted dialkyltryptamines such as 5-MeO-DMT, there remains a need in the art for such compounds with improved oral bioavailability, extended and/or modified pharmacokinetics, in particular for the development of clinically applicable psychedelic drug substances to assist psychotherapy, which may avoid the use of MAOIs. The present invention addresses this need.

SUMMARY OF THE INVENTION

The present invention relates to compounds of formula I, or pharmaceutically acceptable salts thereof, wherein $^xH$, n, $R^1$ and $R^2$ are as defined below.

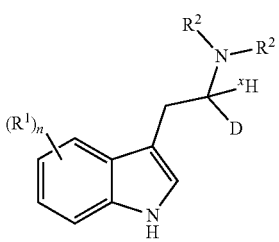

As described above, 5-MeO-DMT is not orally bioavailable without co-administration with an MAOI. The compounds of formula I comprise at least one deuterium atom at the α-position. The inventors have found that such compounds are metabolised surprisingly slowly—substantially more slowly than their α-diprotic analogues—and consequently have improved oral bioavailability. Compounds of formula I are potent tryptamine psychedelics with therapeutic applications in psychiatric or psychocognitive disorders.

Accordingly, viewed from a first aspect, there is provided a compound of formula I, or a pharmaceutically acceptable salt thereof for use in a therapy,

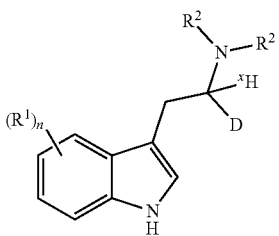

wherein $^xH$ is protium or deuterium,
n is selected from 1, 2, 3 or 4,
$R^1$ is independently selected from $-R^3$, $-OR^3$, $-O(CO)R^3$, $-F$, $-Cl$, $-Br$ or $-I$, and
$R^2$ and $R^3$ are independently selected from $C_1$-$C_4$alkyl.

Viewed from a second aspect, there is provided a compound as defined in the first aspect, or a pharmaceutically acceptable salt thereof, with the proviso that when n is 1 and $R^1$ is 5-methoxy, one $^xH$ is deuterium and the other is protium.

The inventors have applied knowledge of the kinetic isotope effect exhibited by the compounds of the invention in order to modify, controllably, the pharmacokinetic profile of the compounds, thereby permitting more flexible therapeutic application. In particular, by providing individual drug substance compositions comprising mixtures of the compounds of the invention and their undeuterated analogues. Such compositions may enable a finely tuned single dose to maintain a patient in full dissociation from the external world for a therapeutically optimised duration without relying on infusion protocols or combination therapy with monoamine oxidase inhibitors in the clinic.

The inventors have observed a quantifiable relationship between the extent of deuteration and the effect on potentiation of the metabolic half-life of the parent compound. Such a technical effect may be used to quantifiably increase the precision with which compositions comprising pluralities of compounds of formula I may be prepared. By "compositions comprising pluralities of compounds of formula I" is meant compositions comprising at least a first and a second compound wherein the first compound is a compound of formula I and the second compound is an undeuterated analogue of the first compound. For example, the first compound may be α-deutero-5-methoxydimethyltryptamine, in which case the second compound is 5-methoxydimethyltryptamine.

Therefore, viewed from a third aspect, there is provided a composition comprising at least a first and a second compound, or pharmaceutically acceptable salts thereof, wherein the first compound is selected from the compounds defined in the first or second aspects and the second compound is an undeuterated analogue of the first compound.

Viewed from a fourth aspect, there is provided a pharmaceutical composition comprising a compound as defined in the first or second aspects, a pharmaceutically acceptable salt thereof or the composition of the third aspect in combination with a pharmaceutically acceptable excipient.

As described above, the compounds and compositions of the invention have uses in the treatment of psychiatric or neurological disorders. Thus, viewed from a fifth aspect, there is provided a composition of the third or fourth aspects for use in therapy.

Viewed from a sixth aspect, there is provided a compound as defined in the first or second aspects, a pharmaceutically acceptable salt thereof or a composition of the third or fourth aspects for use in a method of treating a psychiatric or neurological disorder in a patient.

Viewed from a seventh aspect, there is provided a method of treatment comprising administering to a patient in need thereof a compound as defined in the first or second aspect, a pharmaceutically acceptable salt thereof or a composition of the third or fourth aspects.

As described above, the compounds of the invention have improved oral bioavailability. Accordingly, viewed from an eighth aspect, there is provided an oral dosage form comprising a compound as defined in the first or second aspect, a pharmaceutically acceptable salt thereof or a composition of the third or fourth aspects.

Further aspects and embodiments of the present invention will be evident from the discussion that follows below.

DETAILED DESCRIPTION OF THE INVENTION

Figure 1:
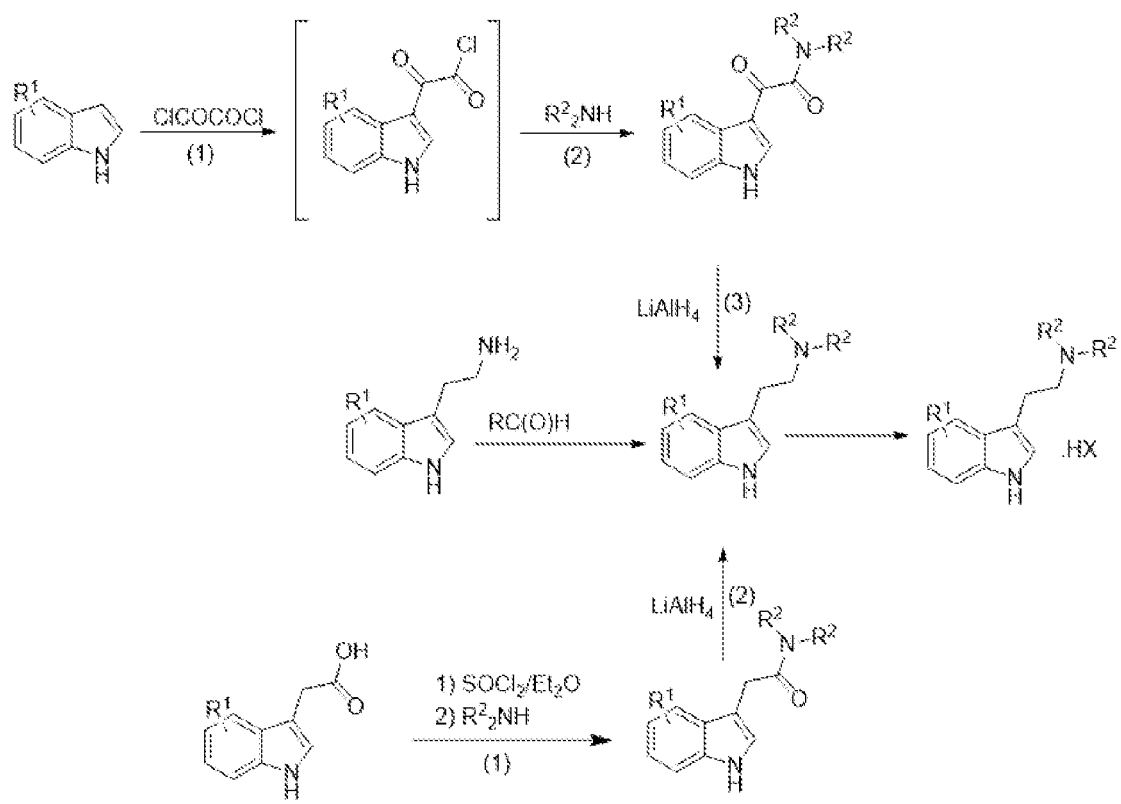
FIG. 1 depicts known synthetic routes for the production of DMT-type compounds.
Figure 2:
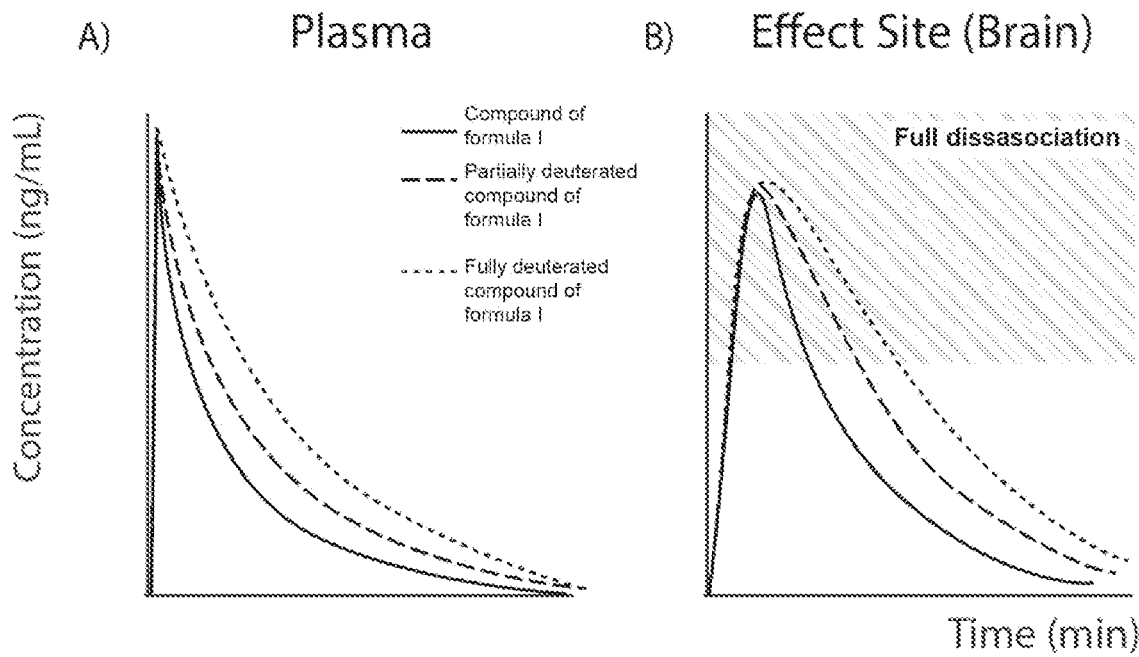
FIG. 2 depicts the predicted pharmacokinetic profile of partially deuterated drug substances of a compound of formula I compared to undeuterated drug substances of a compound of formula I and fully deuterated drug substances of a compound of formula I. Predicted A) plasma concentration and B) brain tissue concentration, showing the extended half-life of partially deuterated DMT. Hashed area depicts effect site concentrations that are experienced as full dissociation from the external world.

Throughout this specification, one or more aspects of the invention may be combined with one or more features described in the specification to define distinct embodiments of the invention.

In the discussion that follows, reference is made to a number of terms, which are to be understood to have the meanings provided below, unless a context expressly indicates to the contrary. The nomenclature used herein for defining compounds, in particular the compounds described herein, is intended to be in accordance with the rules of the International Union of Pure and Applied Chemistry (IUPAC) for chemical compounds, specifically the "IUPAC Compendium of Chemical Terminology (Gold Book)" (see A. D. Jenkins et al., Pure & Appl. Chem., 1996, 68, 2287-2311). For the avoidance of doubt, if a rule of the IUPAC organisation is contrary to a definition provided herein, the definition herein is to prevail.

References herein to a singular of a noun encompass the plural of the noun, and vice-versa, unless the context implies otherwise.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps. The term "comprising" includes within its ambit the term "consisting".

The term "consisting" or variants thereof is to be understood to imply the inclusion of a stated element, integer or step, or group of elements, integers or steps, and the exclusion of any other element, integer or step or group of elements, integers or steps.

The term "about" herein, when qualifying a number or value, is used to refer to values that lie within ±5% of the value specified. For example, if a ratio of coupling agent: compound of formula I is specified to be about 1:1 to about 1.5:1, ratios of 0.95:1 to 1.575:1 are included.

The term "hydrocarbyl" defines univalent groups derived from hydrocarbons by removal of a hydrogen atom from any carbon atom, wherein the term "hydrocarbon" refers to compounds consisting of hydrogen and carbon only. Where a hydrocarbyl is disclosed as optionally comprising one or more heteroatoms, any carbon or hydrogen atom on the hydrocarbyl may be substituted with a heteroatom or a functional group comprising a heteroatom, provided that valency is satisfied. One or more heteroatoms may be selected from the group consisting of nitrogen, sulfur and oxygen.

Oxygen and sulfur heteroatoms or functional groups comprising these heteroatoms may replace —H or —$CH_2$— of a hydrocarbyl, provided that, when —H is replaced, oxygen or the functional group comprising oxygen binds to the carbon originally bound to the —H as either =O (replacing two —H) or —OH (replacing one —H), and sulfur or the functional group comprising sulfur binds to the carbon atom originally bound to the —H as either =S (replacing two —H) or —SH (replacing one —H). When methylene (—$CH_2$—) is replaced, oxygen binds to the carbon atoms originally bound to —$CH_2$— as —O— and sulfur binds to the carbon atoms originally bound to —$CH_2$— as —S—.

Nitrogen heteroatoms or functional groups comprising nitrogen heteroatoms may replace —H, —$CH_2$—, or —CH=, provided that, when —H is replaced, nitrogen or the functional group comprising nitrogen binds to the carbon originally bound to the —H as ≡N (replacing three —H), =NH (replacing two —H) or —$NH_2$ (replacing one —H); when —$CH_2$— is replaced, nitrogen or the functional group comprising nitrogen binds to the carbon atoms originally bound to —$CH_2$— as —NH—; and when —CH= is replaced, nitrogen binds to the carbon atoms originally bound to —CH= as —N=.

The term "alkyl" is well known in the art and defines univalent groups derived from alkanes by removal of a hydrogen atom from any carbon atom, wherein the term "alkane" is intended to define acyclic branched or unbranched hydrocarbons having the general formula $C_nH_{2n+2}$, wherein n is an integer ≥1. $C_1$-$C_4$alkyl refers to any one selected from the group consisting of methyl, ethyl, n-propyl, iso-propyl, n-butyl, sec-butyl, iso-butyl and tert-butyl.

The term "cycloalkyl" defines all univalent groups derived from cycloalkanes by removal of a hydrogen atom from a ring carbon atom. The term "cycloalkane" defines saturated monocyclic and polycyclic branched or unbranched hydrocarbons, where monocyclic cycloalkanes have the general formula $C_nH_{2n}$, wherein n is an integer ≥3. Typically, the cycloalkyl is a $C_5$-$C_6$cycloalkyl, such as cyclopentyl or cyclohexyl.

The term "alkylamino" refers to alkyl groups in which any one hydrogen atom is substituted with a primary (—$NH_2$), secondary (—NRH) or tertiary (—$NR_2$) amino groups, where R is, or each R is independently, a hydrocarbyl group. Typically, any one hydrogen atom is substituted with a tertiary amino group wherein each R is independently a $C_1$-$C_4$alkyl.

The compounds defined in the first aspect and those of the second aspect are useful in therapy and may be administered to a patient in need thereof. As used herein, the term 'patient' preferably refers to a mammal. Typically the mammal is a human, but may also refer to a domestic mammal. The term does not encompass laboratory mammals.

The terms "treatment" and "therapy" define the therapeutic treatment of a patient, in order to reduce or halt the rate of progression of a disorder, or to ameliorate or cure the disorder. Prophylaxis of a disorder as a result of treatment or therapy is also included. References to prophylaxis are intended herein not to require complete prevention of a disorder: its development may instead be hindered through treatment or therapy in accordance with the invention. Typically, treatment or therapy is not prophylactic, and the compounds or compositions are administered to a patient having a diagnosed or suspected disorder.

Psychedelic-assisted psychotherapy means the treatment of a mental disorder by psychological means, which are enhanced by one or more protocols in which a patient is subjected to a psychedelic experience. A psychedelic experience is characterized by the striking perception of aspects of one's mind previously unknown, and may include one or more changes of perception with respect to hallucinations, synesthesia, altered states of awareness or focused consciousness, variation in thought patterns, trance or hypnotic states, and mystical states.

As is understood in the art, psychocognitive, psychiatric or neurological disorders are disorders which may be associated with one or more cognitive impairment. As used herein, the term 'psychiatric disorder' is a clinically significant behavioural or psychological syndrome or pattern that occurs in an individual and that is associated with present distress (e.g., a painful symptom) or disability (i.e., impairment in one or more important areas of functioning) or with a significantly increased risk of suffering death, pain, disability, or an important loss of freedom.

Diagnostic criteria for psychiatric or neurological disorders referred to herein are provided in the Diagnostic and Statistical Manual of Mental Disorders, Fifth Edition, (DSM-5).

As used herein the term 'obsessive-compulsive disorder' (OCD) is defined by the presence of either obsessions or compulsions, but commonly both. The symptoms can cause significant functional impairment and/or distress. An obsession is defined as an unwanted intrusive thought, image or urge that repeatedly enters the person's mind. Compulsions are repetitive behaviours or mental acts that the person feels driven to perform. Typically, OCD manifests as one or more obsessions, which drive adoption of a compulsion. For example, an obsession with germs may drive a compulsion to clean or an obsession with food may drive a compulsion to overeat, eat too little or throw up after eating (i.e. an obsession with food may manifest itself as an eating disorder). A compulsion can either be overt and observable by others, such as checking that a door is locked, or a covert mental act that cannot be observed, such as repeating a certain phrase in one's mind.

The term "eating disorder" includes anorexia nervosa, bulimia and binge eating disorder (BED). The symptoms of anorexia nervosa include eating too little and/or exercising too much in order to keep weight as low as possible. The symptoms of bulimia include eating a lot of food in a very short amount of time (i.e. binging) and then being deliberately sick, using laxatives, eating too little and/or exercising too much to prevent weight gain. The symptoms of BED include regularly eating large portions of food until uncomfortably full, and consequently feeling upset or guilty.

As used herein the term 'depressive disorder' includes major depressive disorder, persistent depressive disorder, bipolar disorder, bipolar depression, and depression in terminally ill patients.

As used herein the term 'major depressive disorder' (MDD, also referred to as major depression or clinical depression) is defined as the presence of five or more of the following symptoms over a period of two-weeks or more (also referred to herein as a 'major depressive episode'), most of the day, nearly every day:

depressed mood, such as feeling sad, empty or tearful (in children and teens, depressed mood can appear as constant irritability);
significantly reduced interest or feeling no pleasure in all or most activities;
significant weight loss when not dieting, weight gain, or decrease or increase in appetite (in children, failure to gain weight as expected);
insomnia or increased desire to sleep;
either restlessness or slowed behaviour that can be observed by others;
fatigue or loss of energy;
feelings of worthlessness, or excessive or inappropriate guilt;
trouble making decisions, or trouble thinking or concentrating;
recurrent thoughts of death or suicide, or a suicide attempt.

At least one of the symptoms must be either a depressed mood or a loss of interest or pleasure.

Persistent depressive disorder, also known as dysthymia, is defined as a patient exhibiting the following two features:
A. has depressed mood for most the time almost every day for at least two years. Children and adolescents may have irritable mood, and the time frame is at least one year.
B. While depressed, a person experiences at least two of the following symptoms:
Either overeating or lack of appetite.
Sleeping too much or having difficulty sleeping.
Fatigue, lack of energy.
Poor self-esteem.
Difficulty with concentration or decision-making.

As used herein the term 'treatment resistant major depressive disorder' describes MDD that fails to achieve an adequate response to an adequate treatment with standard of care therapy.

As used herein, 'bipolar disorder', also known as manic-depressive illness, is a disorder that causes unusual shifts in mood, energy, activity levels, and the ability to carry out day-to-day tasks.

There are two defined sub-categories of bipolar disorder; all of them involve clear changes in mood, energy, and activity levels. These moods range from periods of extremely "up," elated, and energised behaviour (known as manic episodes, and defined further below) to very sad, "down," or hopeless periods (known as depressive episodes). Less severe manic periods are known as hypomanic episodes.

Bipolar I Disorder—defined by manic episodes that last at least 7 days, or by manic symptoms that are so severe that the person needs immediate hospital care. Usually, depressive episodes occur as well, typically lasting at least 2 weeks. Episodes of depression with mixed features (having depression and manic symptoms at the same time) are also possible.

Bipolar II Disorder—defined by a pattern of depressive episodes and hypomanic episodes, but not the full-blown manic episodes described above.

As used herein 'bipolar depression' is defined as an individual who is experiencing depressive symptoms with a previous or coexisting episode of manic symptoms, but does not fit the clinical criteria for bipolar disorder.

As used herein, the term 'anxiety disorder' includes generalised anxiety disorder, phobia, panic disorder, social anxiety disorder, and post-traumatic stress disorder.

'Generalised anxiety disorder' (GAD) as used herein means a chronic disorder characterised by long-lasting anxiety that is not focused on any one object or situation. Those suffering from GAD experience non-specific persistent fear and worry, and become overly concerned with everyday matters. GAD is characterised by chronic excessive worry accompanied by three or more of the following symptoms: restlessness, fatigue, concentration problems, irritability, muscle tension, and sleep disturbance.

'Phobia' is defined as a persistent fear of an object or situation the affected person will go to great lengths to avoid, typically disproportional to the actual danger posed. If the feared object or situation cannot be avoided entirely, the affected person will endure it with marked distress and significant interference in social or occupational activities.

A patient suffering from a 'panic disorder' is defined as one who experiences one or more brief attack (also referred to as a panic attack) of intense terror and apprehension, often marked by trembling, shaking, confusion, dizziness, nausea, and/or difficulty breathing. A panic attack is defined as a fear or discomfort that abruptly arises and peaks in less than ten minutes.

'Social anxiety disorder' is defined as an intense fear and avoidance of negative public scrutiny, public embarrassment, humiliation, or social interaction. Social anxiety often manifests specific physical symptoms, including blushing, sweating, and difficulty speaking.

'Post-traumatic stress disorder' (PTSD) is an anxiety disorder that results from a traumatic experience. Post-traumatic stress can result from an extreme situation, such as combat, natural disaster, rape, hostage situations, child abuse, bullying, or even a serious accident. Common symptoms include hypervigilance, flashbacks, avoidant behaviours, anxiety, anger and depression.

As used herein, the term "post-partum depression" (PPD, also known as postnatal depression) is a form of depression experienced by either parent of a newborn baby. Symptoms typically develop within 4 weeks of delivery of the baby and often include extreme sadness, fatigue, anxiety, loss of interest or pleasure in hobbies and activities, irritability, and changes in sleeping or eating patterns.

As used herein, the term 'substance abuse' means a patterned use of a drug in which the user consumes the substance in amounts or with methods that are harmful to themselves or others.

As used herein, the term 'an avolition disorder' refers to a disorder that includes as a symptom the decrease in motivation to initiate and perform self-directed purposeful activities.

It is to be understood that "LiAl$^x$H$_4$" means the reducing agent (an agent capable of decreasing the oxidation level of an organic compound) lithium aluminium hydride when x is 1, so $^x$H is protium (hydrogen with atomic mass of 1), or lithium aluminium deuteride when x is 2, so $^x$H is deuterium (hydrogen with atomic mass of 2). According to some embodiments, "LiAl$^x$H$_4$" means LiAlD$_4$ or LiAlH$_4$ and LiAlD$_4$. According to some embodiments, "LiAl$^x$H$_4$" is LiAlD$_4$ optionally comprising between 0.1 and 99.9% LiAlH$_4$. Stage 2 of the method disclosed herein comprises reacting the compound of formula II with LiAlD$_4$ or LiAlH$_4$ and LiAlD$_4$, i.e., LiAlD$_4$ or mixtures of LiAlH$_4$ and LiAlD$_4$ may be reacted with the compound of formula II. Mixtures of between 2% and 98% lithium aluminium hydride or between 2% and 98% lithium aluminium deuteride may be employed.

Unless context indicates otherwise, amine means secondary amine.

High-performance liquid chromatography (HPLC), is a technique in analytical chemistry used to separate, identify, and quantify each component in a mixture. For a review of HPLC, see A. M. Sabir et al., *Int. Res. J. Pharm.*, 2013, 4, 4, 39-46.

Solvents referred to herein include MeCN (acetonitrile), DCM (dichloromethane), acetone, IPA (isopropyl alcohol), iPrOAc (isopropyl acetate), TBME (t-butyl methyl ether), THF (tetrahydrofuran), 2-MeTHF (2-methyl tetrahydrofuran), EtOAc (ethyl acetate), ethanol and toluene. As used herein, the term ether solvent means a solvent containing an alkyl-O-alkyl moiety, wherein the two alkyl components may be connected. Ether solvents include diethyl ether, TBME, THF and 2-MeTHF.

A drying agent is a chemical used to remove water from an organic compound that is in solution. Examples of drying agents include calcium chloride, magnesium sulphate, and sodium sulphate. Drying agents described herein are typically magnesium sulphate.

An acidic reagent suitable for crystallising a pharmaceutically acceptable salt of a compound of formula I is an acid which forms a non-toxic acid anion. Examples include hydrochloride, hydrobromide, sulphate, phosphate or acid phosphate, acetate, maleate, fumarate, lactate, tartrate, citrate and gluconate.

Aqueous basic solution means a mild base suitable for workup, for example a 10% potassium carbonate solution.

As described above, the invention provides in its first aspect a compound of formula I, or a pharmaceutically acceptable salt thereof for use in therapy,

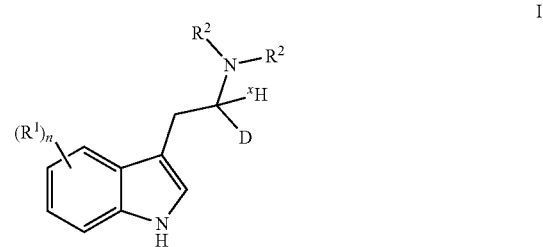

I wherein $^x$H is protium or deuterium,
n is selected from 1, 2, 3 or 4,
R$^1$ is independently selected from —R$^3$, —OR$^3$, —O(CO)R$^3$, —F, —Cl, —Br or —I, and
R$^2$ and R$^3$ are independently selected from C$_1$-C$_4$alkyl.
R$^2$ is independently selected from C$_1$-C$_4$alkyl, and is often independently selected from methyl or ethyl. In some embodiments, R$^2$ is methyl.
R$^1$ is independently selected from —R$^3$, —OR$^3$, —O(CO)R$^3$, —F, —Cl, —Br or —I, and R$^3$ is selected from C$_1$-C$_4$alkyl. Often, R$^1$ is independently selected from —OR$^3$, and —O(CO)R$^3$. Often, R$^3$ is methyl or ethyl. In some embodiments, R$^3$ is methyl. In some embodiments, R$^1$ is methoxy or acetoxy, such as methoxy.

In some embodiments, n is 1 to 4. In some embodiments, wherein n is >1, at least one R$^1$ is at the 4- or 5-position.

In some embodiments, n is 0 or 1. In some embodiments, n is 0. In other embodiments, n is 1. In some embodiments, n is 1 and R$^1$ is at the 4- or 5-position.

In some embodiments, n is 1 and R$^1$ is selected from —OR$^3$ and —O(CO)R$^3$, typically wherein R$^3$ is methyl. Often, R$^1$ is —OR$^3$, typically wherein R$^3$ is methyl (i.e. R$^1$ is often OMe).

In some embodiments, when n is 1, R$^1$ is selected from 4-methoxy (4-MeO), 5-MeO, 4-acetoxy (4-AcO), and 5-AcO, such as 5-methoxy.

In some embodiments, $^x$H is deuterium.

In more specific embodiments of the first aspect, the compound of formula I is α,α-dideutero-5-methoxydimethyltryptamine.

Methods by which the compounds of formula I may be produced are described below and are suitable for the production of high purity compounds of formula I. In some embodiments, the compound of formula I, or a pharmaceutically acceptable salt thereof, is of a purity of between 99% and 100% by HPLC, such as a purity of between 99.5% and 100% by HPLC. In some embodiments, the compound of formula I, or a pharmaceutically acceptable salt thereof, is of a purity of between 99.9% and 100% by HPLC, such as a purity of between 99.95% and 100% by HPLC.

In some embodiments, the compound of formula I, or a pharmaceutically acceptable salt thereof, produces two or fewer impurity peaks by HPLC. In some embodiments, where the compound of formula I, or a pharmaceutically acceptable salt thereof, produces impurity peaks by HPLC, no impurity peak is greater than 0.2%. In some embodiments, no impurity peak by HPLC is greater than 0.1%.

In some embodiments, the compound of formula I is in the form of a pharmaceutically acceptable salt. The pharmaceutically acceptable salt often comprises a compound of formula I and a suitable acid. The compound of formula I is typically protonated at —N(R$^2$)$_2$, forming —[NH(R$^2$)$_2$]$^+$, and the resultant positive charge is countered by an anion.

P. H. Stahl and C. G. Wermuth provide an overview of pharmaceutical salts and the acids comprised therein in Handbook of Pharmaceutical Salts: Properties, Selection and Use, Weinheim/Zürich:Wiley-VCH/VHCA, 2002. The acids described in this review are suitable components of the pharmaceutically acceptable salt of formula I.

In some embodiments, the acid is any one selected from the group consisting of fumaric acid, tartaric acid, citric acid, hydrochloric acid, acetic acid, lactic acid, gluconic acid, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, adipic acid, ascorbic acid, aspartic acid, benzenesulfonic acid, benzoic acid, camphoric acid, camphor-10-sulfonic acid, decanoic acid, hexanoic acid, octanoic acid, carbonic acid, cinnamic acid, cyclamic acid, dodecylsulfuric acid, ethane-1,2-disulfonic acid, ethanesulfonic acid, formic acid, galactaric acid, gentisic acid, glucoheptonic acid, glucuronic acid, glutamic acid, glutaric acid, glycerophosphoric acid, glycolic acid, hippuric acid, hydrobromic acid, isobutyric acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (-L), salicylic acid, sebacic acid, stearic acid, succinic acid, sulfuric acid, thiocyanic acid, toluenesulfonic acid and undecylenic acid.

Often, the acid is any one selected from fumaric acid, tartaric acid, citric acid and hydrochloric acid. In some embodiments, the acid is fumaric acid, i.e. the pharmaceutically acceptable salt is a fumarate salt.

As described above, the invention provides in its second aspect a compound of formula I, or a pharmaceutically acceptable salt thereof,

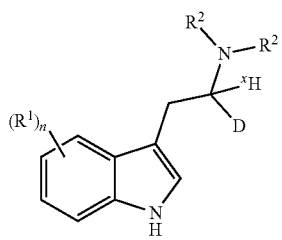

I wherein $^x$H is protium or deuterium,
n is selected from 1, 2, 3 or 4,
R$^1$ is independently selected from —R$^3$, —OR$^3$, —O(CO)R$^3$, —F, —Cl, —Br or —I, and R$^2$ and R$^3$ are independently selected from C$_1$-C$_4$alkyl, with the proviso that when n is 1 and R$^1$ is 5-methoxy, one $^x$H is deuterium and the other is protium.

For the avoidance of doubt, embodiments related to the compound of formula I, or a pharmaceutically acceptable salt thereof, of the first aspect of the invention also apply mutatis mutandis to the second aspect, provided that when n is 1 and R$^1$ is 5-methoxy, one $^x$H is deuterium and the other is protium. For example, R$^2$ of the compound of formula I or pharmaceutically acceptable salt thereof may be methyl; R$^1$ may be methoxy or acetoxy; and/or n may be 1 and R$^1$ may be at the 4- or 5-position.

Also disclosed herein is a synthetic method for making a compound of formula I or a pharmaceutically acceptable salt thereof. The method comprises stage 1 and stage 2, wherein stage 1 comprises:
(i) reacting a compound of formula III with two or more coupling agents to produce an activated compound;
(ii) reacting the activated compound with an amine having the formula (R$^2$)$_2$NH to produce a compound of formula II;
and wherein stage 2 comprises reacting the compound of formula II with LiAlD$_4$ or LiAlH$_4$ and LiAlD$_4$,

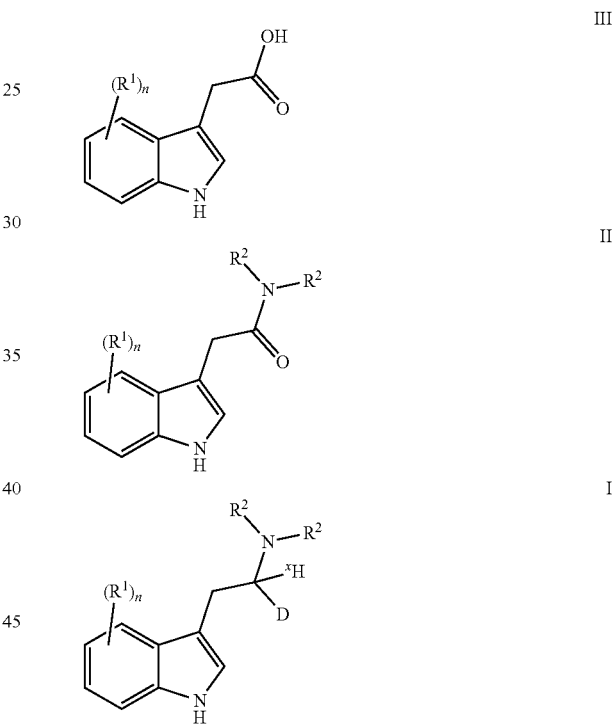

wherein $^x$H is protium or deuterium,
n is selected from 1, 2, 3 or 4,
R$^1$ is independently selected from —R$^3$, —OR$^3$, —O(CO)R$^3$, —F, —Cl, —Br or —I, and
R$^2$ and R$^3$ are independently selected from C$_1$-C$_4$alkyl.

For the avoidance of doubt, embodiments related to the compound of formula I, or a pharmaceutically acceptable salt thereof, of the first aspect of the invention also apply mutatis mutandis to the compound of formula I (and thus compounds of formulae III and II) of the synthetic method. For example, R$^2$ of the compound of formula I or pharmaceutically acceptable salt thereof (and thus also the compound of formula II and the amine having the formula (R$^2$)$_2$NH) may be methyl; R$^1$ of the compound of formula I (and thus also of formulae III and II) may be methoxy or acetoxy; and/or n may be 1 and R$^1$ may be at the 4- or 5-position.

The synthetic method avoids the use of problematic oxalyl chloride and employs compounds of formula II, which may be derived from auxin derivatives. High quality and purity auxins of formula III are commercially available at scale and/or can be readily synthesised via the Fischer synthesis, Bartoli synthesis, Japp-Klingemann synthesis or Larock synthesis (see, for example, M. B. Smith and J. March, 2020, *March's Advanced Organic Chemistry*, $8^{th}$ edition, Wiley, New Jersey). The method is efficient, scalable, compatible with Current Good Manufacturing Practices (cGMP), and is suitable for the production of high purity compounds of formula I. For example, the method is suitable for the production of compounds of formula I in batch scales ranging from 1 g to 100 kg and is suitable for the production of compounds of formula I with a purity of >99.9% and overall yield of 65% or more.

The compound of formula II is produced on reacting a compound of formula III with two or more coupling agents to produce an activated compound, and reacting the activated compound with an amine having the formula $(R^2)_2NH$. Without wishing to be bound by theory, it is understood that the nitrogen atom of the amine binds to the carbon atom of the carbonyl of formula III, resulting in the formation of the compound of formula II. For the avoidance of doubt, the $R^2$ groups of formulae II and I are derived from the $R^2$ groups of the amine. Thus, as described above, $R^2$ of formulae II and I is independently selected from $C_1$-$C_4$alkyl, is often independently selected from methyl or ethyl and in some embodiments, $R^2$ is methyl.

The compound of formula I is produced on reacting the compound of formula II with $LiAlD_4$ or $LiAlH_4$ and $LiAlD_4$. Without wishing to be bound by theory, it is understood that the hydride or deuteride ions provided by $LiAlD_4$ or $LiAlH_4$ and $LiAlD_4$ bind to the carbon atom of the carbonyl of formula II, resulting in the formation of the compound of formula I. For the avoidance of doubt, the $^xH$ groups of formula I are derived from the hydride or deuteride ions provided by $LiAlD_4$ or $LiAlH_4$ and $LiAlD_4$.

As described above, the method comprises stage 1 and stage 2. Stage 1 comprises:
(i) reacting a compound of formula III with two or more coupling agents to produce an activated compound; and
(ii) reacting the activated compound with an amine having the formula $(R^2)_2NH$ to produce a compound of formula II.

The term "coupling agent" refers to an agent which facilitates the chemical reaction between an amine and a carboxylic acid. The two or more coupling agents may comprise a carboxylic acid activating agent, i.e. an agent which reacts with the carboxylic acid moiety of formula III to produce a compound comprising an activated moiety derived from the original carboxylic acid moiety that is more likely to react with an amine than the original carboxylic acid moiety.

The activated compound is the product of the reaction between the compound of formula III and the two or more coupling agents. Where the two or more coupling agents comprise carboxylic acid activating agents, the activated compound comprises an activated moiety, derived from the original carboxylic acid moiety of formula III, which is more likely to react with an amine than the original carboxylic acid moiety.

The two or more coupling agents may comprise a carboxylic acid activating agent. The two or more coupling agents may comprise an additive coupling agent.

An additive coupling agent (also referred to herein as an "additive") is an agent which enhances the reactivity of a coupling agent. The additive may be a compound capable of reacting with the product of the reaction of formula III and the coupling agent (the product being a compound comprising an activated moiety) to produce a compound comprising an even more activated moiety that is more likely to react with an amine than the original activated moiety.

The additive may be capable of reacting with the product of the reaction of formula III and the coupling agent (the product being a compound comprising an activated moiety) to produce an activated compound comprising an even more activated moiety that is more likely to react with an amine than the original activated moiety.

Often, the two or more coupling agents comprise a carboxylic acid activating agent and an additive coupling agent.

At least one of the two or more coupling agents may be selected from the group consisting of carbodiimide coupling agents, phosphonium coupling agents and 3-(diethoxy-phosphoryloxy)-1,2,3-benzo[d]triazin-4(3H)-one (DEPBT), such as a carbodiimide coupling agent or a phosphonium coupling agent. At least one of the two or more coupling agents may be a carbodiimide coupling agent.

A carbodiimide coupling agent is a coupling agent which comprises a carbodiimide group R'—N=C=N—R", wherein R' and R" are hydrocarbyl groups optionally substituted with heteroatoms selected from nitrogen, sulfur and oxygen, typically nitrogen. Often, R' and R" are independently selected from $C_1$-$C_6$alkyl, $C_5$-$C_6$cycloalkyl, $C_1$-$C_6$alkylamino and morpholino$C_1$-$C_6$alkyl. Often, $C_1$-$C_6$alkyl is $C_3$alkyl, $C_5$-$C_6$cycloalkyl is cyclohexyl, $C_1$-$C_6$alkylamino is dimethylaminopropyl and/or morpholino$C_1$-$C_6$alkyl is morpholinoethyl.

The carbodiimide coupling agent may be any one selected from the group consisting of dicyclohexylcarbodiimide (DCC), diisopropylcarbodiimide (DIC), (N-(3-Dimethylaminopropyl)-N'-ethylcarbodiimide (EDC) and 1-cyclohexyl-(2-morpholinoethyl)carbodiimide metho-p-toluene sulfonate (CMCT). The carbodiimide coupling agent may be any one selected from the group consisting of dicyclohexylcarbodiimide (DCC), diisopropylcarbodiimide (DIC) and (N-(3-Dimethylaminopropyl)-N'-ethylcarbodiimide (EDC). Often, the carbodiimide coupling agent is N-(3-Dimethylaminopropyl)-N'-ethylcarbodiimide (EDC), typically as a hydrochloride salt (EDC.HCl). EDC or EDC.HCl are particularly preferred as they are non-toxic and are highly water soluble, facilitating their virtually complete removal in workup and wash steps of stage 1.

A phosphonium coupling agent comprises a phosphonium cation and a counterion, typically a hexafluorophosphate anion. The phosphonium cation may be of formula $[PR^a_3R^b]^+$ wherein $R^a$ is di($C_1$-$C_6$)alkylamino or pyrrolidinyl and $R^b$ is halo or a hydrocarbyl group optionally substituted with nitrogen and/or oxygen atoms. Often, $R^b$ is bromo, benzotriazol-1-yloxy or 7-aza-benzotriazol-1-yloxy.

The phosphonium coupling agent may be any one selected from the group consisting of benzotriazol-1-yloxy-tris(dimethylamino)-phosphonium hexafluorophosphate (BOP), bromo-tripyrrolidino-phosphonium hexafluorophosphate (PyBrOP), benzotriazol-1-yloxy-tripyrrolidino-phosphonium hexafluorophosphate (PyBOP), 7-aza-benzotriazol-1-yloxy-tripyrrolidinophosphonium hexafluorophosphate (PyAOP) and ethyl cyano(hydroxyimino)acetato-$O_2$) tri-(1-pyrrolidinyl)-phosphonium hexafluorophosphate (PyOxim).

At least one of the two or more coupling agents may be an additive coupling agent selected from the group consisting of 1-hydroxybenzotriazole (HOBt), hydroxy-3,4-dihydro-4-oxo-1,2,3-benzotriazine (HOOBt), N-hydroxysuccinimide (HOSu), 1-hydroxy-7-azabenzotriazole (HOAt), ethyl 2-cyano-2-(hydroximino)acetate (Oxyma Pure), 4-(N,N-Dimethylamino)pyridine (DMAP), N-hydroxy-5-norbornene-2,3-dicarboximide (HONB), 6-chloro-1-hydroxybenzotriazole (6-Cl-HOBt), 3-hydroxy-4-oxo-3,4-dihydro-1,2,3-benzotriazine (HODhbt), 3-hydroxy-4-oxo-3,4-dihydro-5-azabenzo-1,2,3-triazene (HODhat) and 3-hydroxyl-4-oxo-3,4-dihydro-5-azepine benzo-1,3-diazines (HODhad).

At least one of the two or more coupling agents may be an additive coupling agent selected from the group consisting of 1-hydroxybenzotriazole (HOBt), hydroxy-3,4-dihydro-4-oxo-1,2,3-benzotriazine (HOOBt), N-hydroxysuccinimide (HOSu), 1-hydroxy-7-azabenzotriazole (HOAt), ethyl 2-cyano-2-(hydroximino)acetate (Oxyma Pure) and 4-(N,N-Dimethylamino)pyridine (DMAP).

At least one of the two or more coupling agents may be an additive coupling agent which is 1-hydroxybenzotriazole.

The two or more coupling agents may consist of a coupling agent and an additive coupling agent wherein the coupling agent and additive coupling agent may be as described in the above embodiments.

A benefit of using both a coupling agent and an additive coupling agent is an increased rate of formation of compounds of formula II from compounds of formula III and an amine having the formula $(R^2)_2NH$. In addition, when an additive coupling agent is used together with a carbodiimide coupling agent, the likelihood of unwanted side reactions may be reduced. For example, reaction of a compound of formula III with a carbodiimide coupling reagent is likely to form an O-acylisourea. This may undergo a rearrangement to form an N-acylurea, which is a stable compound unlikely to react with an amine. Additive coupling reagents may react with O-acylureas before rearrangement to N-acylureas, and produce compounds that go on to react with an amine, rather than inactive N-acylureas.

Therefore, the two or more coupling agents may consist of a carbodiimide coupling agent and an additive coupling agent.

The two or more coupling agents may consist of N-(3-Dimethylaminopropyl)-N'-ethylcarbodiimide (EDC), typically as a hydrochloride salt (EDC.HCl), and 1-hydroxybenzotriazole (HOBt).

Often, an excess of coupling agent with respect to compound of formula III is used. The ratio of coupling agent:compound of formula III may be about 1:1 to about 3:1, typically about 1:1 to about 2:1 and most typically about 1:1 to about 1.5:1.

Often, an excess of additive coupling agent with respect to compound of formula III is used. Sometimes, the ratio of additive coupling agent:compound of formula III is about 1:1 to about 3:1, typically about 1:1 to about 2:1 and most typically about 1:1 to about 1.5:1.

Where the two or more coupling agents comprise a coupling agent and an additive coupling agent, a ratio of coupling agent:compound of formula III and additive coupling agent:compound of formula III of about 1:1 to about 1.5:1 may be used.

As described above, stage 1 comprises reacting the activated compound (the product of reacting a compound of formula III with two or more coupling agents) with an amine having the formula $(R^2)_2NH$ to produce a compound of formula II. $R^2$ is independently selected from $C_1$-$C_4$alkyl. Often, $R^2$ is independently selected from methyl or ethyl. Typically, $R^2$ is methyl, i.e. the amine is dimethylamine.

The ratio of amine:compound of formula III employed in the method is often about 21:1. Sometimes, the ratio of amine:compound of formula II is about 1:1 to about 3:1, typically about 1:1 to about 2:1.

Sometimes, stage 1 further comprises isolating the compound of formula II. The skilled person is aware of techniques in the art suitable for isolation of a compound of formula II. For example, a compound of formula II may be extracted into an organic solvent such as dichloromethane or ethyl acetate, washed with an aqueous solution such as an aqueous basic solution, and concentrated. To increase purity, the isolated compound of formula II may be recrystallized. The skilled person is aware of techniques that are suitable for recrystallisation of compounds of formula II. For example, the compound of formula II may be dissolved in the minimum amount of solvent at a particular temperature (e.g. at ambient temperature (e.g. 15 to 25° C.) or at elevated temperatures where heat is applied to the solution) and the resultant solution cooled to encourage precipitation. Alternatively, or in addition, the volume of the solution may be reduced to encourage precipitation, e.g. by simple evaporation at ambient temperature and pressure. Alternatively, or in addition, an anti-solvent may be used (in which the compound of formula II is less soluble than the solvent already present).

Isolated compounds of formula II are stable and may be stored as solids at ambient temperature, e.g. at about 20° C., in the air. They may, but need not be, stored under inert conditions, e.g. under nitrogen or argon, or at reduced temperatures, e.g. in a refrigerator or freezer.

Typically, steps (i) and (ii) of stage 1 are carried out in a suitable solvent. The skilled person is able to assess which solvents are suitable for these steps. Examples of suitable solvents include dichloromethane (DCM), acetone, isopropyl alcohol (IPA), isopropyl acetate (iPrOAc), tert-butyl methyl ether (TBME), 2-methyl tetrahydrofuran (2-MeTHF) and ethyl acetate (EtOAc). In some embodiments, steps (i) and (ii) of stage 1 are carried out in dichloromethane.

Steps (i) and (ii) of stage 1 are carried out at a suitable temperature and the skilled person is able to assess which temperatures are suitable for these steps. Often, steps (i) and (ii) of stage 1 are carried out at temperatures of about 10° C. to about 30° C. In some embodiments, steps (i) and (ii) of stage 1 are carried out at room temperature (about 20° C.).

Sometimes, stage 1 of the method comprises the steps of:
i. contacting a compound of formula III and between 1 and 1.5 equivalents of an additive coupling agent, and between 1 and 1.5 equivalents of a carbodiimide coupling agent to produce a first composition; and
ii. contacting the first composition with between 1 and 2 equivalents of an amine having the formula $(R^2)_2NH$ to produce a second composition.

Often, 1 g or more, such as 1 g to 100 kg or 1 g to 1 kg of a compound of formula III is employed in the method.

The contacting of steps i. and ii. is often carried out in the presence of a first solvent, such as between 5 and 20 volumes of a first solvent. The first solvent may be selected from any one of dichloromethane (DCM), acetone, isopropyl alcohol (IPA), isopropyl acetate (iPrOAc), tert-butyl methyl ether (TBME), 2-methyl tetrahydrofuran (2-MeTHF) and ethyl acetate (EtOAc). Typically, the first solvent is DCM.

Often, step i. further comprises stirring or agitating the first composition. The first composition may be stirred or agitated for at least 30 minutes, such as 30 minutes to 3 hours or 30 minutes to 2 hours, preferably at least 1 hour, for example 1 to 3 hours or 1 to 2 hours. The first composition may be maintained at a temperature of between 10° C. and 30° C.

The amine of step ii. is often dissolved in a solvent, such as tetrahydrofuran (THF) or ether, prior to contacting. The amine may be present in the solvent at a concentration of about 2 M. Typically, the amine of step ii. is dissolved in THF.

Sometimes, step ii. further comprises stirring or agitating the second composition. The second composition may be stirred or agitated for at least 30 minutes, such as 30 minutes to 3 hours or 30 minutes to 2 hours, preferably at least 1 hour, for example 1 to 3 hours or 1 to 2 hours. The second composition may be maintained at a temperature of between 10° C. and 30° C.

Step ii. may further comprise contacting the second composition with an aqueous basic solution to produce a third composition, for example contacting the second composition with between 2 and 10 volumes of an aqueous basic solution such as an aqueous solution comprising potassium carbonate.

Sometimes, step ii. further comprises stirring or agitating the third composition. The third composition may be stirred or agitated for at least 1 minute, such as 1 to 15 minutes or 1 to 10 minutes, preferably at least 5 minutes, for example 5 to 15 minutes or 5 to 10 minutes. The third composition may be maintained at a temperature of between 10° C. and 30° C.

Where the third composition comprises an organic and an aqueous component, step ii. may further comprise separating the organic component from the aqueous component. The organic component may be separated from the aqueous component within 8 hours of the contacting of step i.

Sometimes, stage 1 of the method comprises the steps of:
i. adding to a first vessel 1 g or more of a compound of formula III and between 1 and 1.5 equivalents of an additive coupling agent,
ii. adding to the first vessel between 5 and 20 volumes of a first solvent selected from DCM, acetone, IPA, iPrOAc, TBME, 2-MeTHF and EtOAc,
iii. adding to the first vessel between 1 and 1.5 equivalents of a carbodiimide coupling agent,
iv. stirring the contents of the first vessel for at least 30 minutes, preferably at least 1 hour (such as 1 to 2 hours), at between 10° C. and 30° C.,
v. adding to the first vessel between 1 and 2 equivalents of an amine having the formula $(R^2)_2NH$, wherein the amine is preferably dissolved in an ether solvent,
vi. further stirring the contents of the first vessel for at least 30 minutes, preferably at least 1 hour (such as 1 to 2 hours), at between 10° C. and 30° C.,
vii. adding to the first vessel between 2 and 10 volumes of an aqueous basic solution,
viii. further stirring the contents of the first vessel for at least 1 minute, preferably at least 5 minutes (such as 5 to 10 minutes), at between 10° C. and 30° C.,
ix. allowing an immiscible organic fraction to separate from an aqueous fraction, wherein the organic fraction comprises the compound of formula II, and
x. removing the organic fraction comprising the compound of formula II,
wherein steps i. to x. are carried out within a single 8 hour period.

Often, the first solvent is DCM.

Often, the amine is dimethylamine. The amine may be dissolved in THF, for example at a concentration of 2 M.

Often, the aqueous basic solution comprises potassium carbonate.

Sometimes, stage 1 of the method further comprises the steps of:
xi. drying the organic fraction with a drying agent, for example a drying agent selected from calcium chloride, magnesium sulphate, and sodium sulphate,
xii. filtering the organic fraction,
xiii. concentrating the organic fraction, for example under vacuum such as under a pressure of less than 1 atmosphere,
xiv. adding the concentrated organic fraction to a second vessel,
xv. adding between 2 and 10 volumes of a second solvent to the second vessel, wherein the second solvent is selected from IPA, EtOAc, IPrOAc, acetonitrile (MeCN), TBME, THF, 2-MeTHF and toluene,
xvi. stirring the contents of the second vessel for at least 1 hour, preferably at least 2 hours (such as 2 to 3 hours), at temperatures of between 45° C. and 55° C.,
xvii. cooling the contents of the second vessel to temperatures of between 15° C. and 25° C.,
xviii. filtering contents of the second vessel to obtain a filtrate, wherein the filtrate comprises the compound of formula II, and
xix. drying the filtrate.

The drying agent of step xi. is typically magnesium sulphate. Often, the solvent of step xv. is selected from TBME and IPA.

Stage 2 of the method comprises reacting the compound of formula II with $LiAlD_4$ or $LiAlH_4$ and $LiAlD_4$ to produce a compound of formula I. $LiAlD_4$ or mixtures of $LiAlH_4$ and $LiAlD_4$ may be reacted with the compound of formula II. In preferred embodiments, stage 2 of the method comprises reacting the compound of formula II with a mixture of $LiAlH_4$ and $LiAlD_4$. Such mixtures comprise $LiAlD_4$ and comprise between 0.1 and 99.9% hydride. Mixtures of between 2% and 98% lithium aluminium hydride or between 2% and 98% lithium aluminium deuteride may be employed. Sometimes, mixtures of $LiAlH_4$ and $LiAlD_4$ consist essentially of 98% $LiAlD_4$/2% $LiAlH_4$. Sometimes, such mixtures consist essentially of 95% $LiAlD_4$/5% $LiAlH_4$, 95% $LiAlD_4$/5% $LiAlH_4$, 85% $LiAlD_4$/15% $LiAlH_4$, 80% $LiAlD_4$/20% $LiAlH_4$, 75% $LiAlD_4$/25% $LiAlH_4$, 70% $LiAlD_4$/30% $LiAlH_4$, 65% $LiAlD_4$/35% $LiAlH_4$, 60% $LiAlD_4$/40% $LiAlH_4$, 55% $LiAlD_4$/45% $LiAlH_4$, 50% $LiAlD_4$/50% $LiAlH_4$, 45% $LiAlD_4$/55% $LiAlH_4$, 40% $LiAlD_4$/60% $LiAlH_4$, 35% $LiAlD_4$/65% $LiAlH_4$, 30% $LiAlD_4$/70% $LiAlH_4$, 25% $LiAlD_4$/75% $LiAlH_4$, 20% $LiAlD_4$/80% $LiAlH_4$, 15% $LiAlD_4$/85% $LiAlH_4$, 10% $LiAlD_4$/90% $LiAlH_4$, 5% $LiAlD_4$/95% $LiAlH_4$, or 2% $LiAlD_4$/98% $LiAlH_4$.

By the mixtures of $LiAlH_4$ and $LiAlD_4$ consisting essentially of specified percentages of $LiAlH_4$ and $LiAlD_4$ is meant that the mixture may comprise additional components (other than $LiAlH_4$ and $LiAlD_4$) but that the presence of these additional components will not materially affect the essential characteristics of the mixture. In particular, mixtures consisting essentially of $LiAlH_4$ and $LiAlD_4$ will not comprise material amounts of agents that are detrimental to the reduction of compounds of formula II to produce compounds of formula I (e.g. material amounts of agents that react with $LiAlH_4$ and $LiAlD_4$, compounds of formula II and/or compounds of formula I in a way that inhibits the reduction of compounds of formula II to produce compounds of formula I).

The amount of $LiAlH_4$ or $LiAlD_4$ comprised in mixtures of the two depends on the degree of deuteration sought in the compound of formula I. For example, where compounds of formula I are sought in which one $^xH$ is protium and the other is deuterium, a mixture of 50% $LiAlH_4$ and 50% $LiAlD_4$ may be preferred. Alternatively, where a mixture of compounds of formula I are sought, in which approximately half of the compounds comprise two deuterium atoms at the α-position (i.e. both $^xH$ are deuterium) and approximately half of the compounds comprise one deuterium atom and one protium atom at the α-position (i.e. one $^xH$ is deuterium and the other is protium), a mixture of 25% $LiAlH_4$ and 75% $LiAlD_4$ may be preferred.

The amount of $LiAlD_4$ or $LiAlH_4$ and $LiAlD_4$ employed relative to compound of formula II is often ≤1:1. For the avoidance of doubt, the ratios of $LiAlD_4$ or $LiAlH_4$ and $LiAlD_4$ relative to compound of formula II refer to the total amount of $LiAlD_4$ or $LiAlH_4$ and $LiAlD_4$ used with respect to the amount of compound II. Sometimes, the ratio of $LiAlD_4$ or $LiAlH_4$ and $LiAlD_4$:compound of formula II is 0.5:1 to 1:1, such as 0.8:1 to 1:1. Typically, the ratio of $LiAlH_4$ and/or $LiAlD_4$:compound of formula II is 0.9:1.

Typically, stage 2 of the method is carried out in a suitable solvent. The skilled person is able to assess which solvents are suitable for stage 2. Examples of suitable solvents include ethers such as THF and diethyl ether. Often, stage 2 is carried out in THF.

Often, the $LiAlD_4$ or $LiAlH_4$ and $LiAlD_4$ is provided as a solution or suspension of $LiAlD_4$ or $LiAlH_4$ and $LiAlD_4$ in a suitable solvent such as an ether, for example THF or diethyl ether, typically THF.

Stage 2 of the method is carried out at a suitable temperature and the skilled person is able to assess which temperatures are suitable for these steps. Often, stage 2 is carried out at temperatures of about −5° C. to about 65° C.

Typically, stage 2 further comprises isolating the compound of formula I. The skilled person is aware of techniques in the art suitable for isolation of a compound of formula I. For example, on quenching the reaction (e.g. with an aqueous solution of a tartrate salt such as Rochelle's salts), a compound of formula I may be extracted into an organic solvent such as an ether, e.g. THF or diethyl ether, washed with an aqueous solution such as an aqueous basic solution, and concentrated. The isolated compound of formula I may be recrystallized. The skilled person is aware of techniques that are suitable for recrystallisation of a compound of formula I. The examples of recrystallisation techniques described with respect to recrystallisation of a compound of formula II apply mutatis mutandis to recrystallisation of a compound of formula I.

Often, about 1 g or more, such as about 1 g to about 100 kg or about 1 g to about 1 kg of a compound of formula II is employed in the method.

Typically, stage 2 of the method comprises contacting a compound of formula II and between about 0.8 and about 1 equivalents, such as about 0.9 equivalents of $LiAlD_4$ or $LiAlH_4$ and $LiAlD_4$ to produce a first composition.

The contacting is typically carried out in the presence of a solvent such as an ether, e.g. THF or diethyl ether, typically THF.

Often, the contacting comprises dropwise addition of $LiAlD_4$ or $LiAlH_4$ and $LiAlD_4$ to a compound of formula II, wherein $LiAlD_4$ or $LiAlH_4$ and $LiAlD_4$ is provided as a solution or suspension of $LiAlD_4$ or $LiAlH_4$ and $LiAlD_4$ in a suitable solvent, such as an ether, e.g. THF or diethyl ether. The $LiAlD_4$ or $LiAlH_4$ and $LiAlD_4$ may be provided as a 2.4 M or 2 M solution or suspension of $LiAlD_4$ or $LiAlH_4$ and $LiAlD_4$ in THF. Sometimes, the $LiAlD_4$ or $LiAlH_4$ and $LiAlD_4$ is provided as a 2 M solution or suspension of $LiAlD_4$ or $LiAlH_4$ and $LiAlD_4$ in THF.

The contacting is often carried out at temperatures of about −5° C. to about 65° C.

Often, stage 2 further comprises stirring or agitating the first composition. The first composition may be stirred or agitated for about 1 hour to about 6 hours, typically for about 2 hours. The first composition may be stirred or agitated at a temperature of about 55° C. to about 65° C. Often, the first composition is stirred or agitated at a temperature of about 55° C. to about 65° C. and then cooled to temperatures of about 10° C. to about 30° C.

Typically, the compound of formula II is contacted with about 0.9 equivalents of $LiAlD_4$ or $LiAlH_4$ and $LiAlD_4$.

Stage 2 of the method of the invention may comprise the steps of:

i. adding to a third vessel 1 g or more (such as 1 g to 1 kg) of a compound of formula II,
ii. adding to the third vessel between 5 and 20 volumes of an ether solvent,
iii. adding to the third vessel, dropwise over at least 15 minutes (e.g. 15 to 30 minutes), a solution of between 0.8 and 1 equivalents of $LiAlD_4$ or $LiAlH_4$ and $LiAlD_4$ in the ether solvent at a temperature of between −5° C. and 65° C.,
iv. stirring the contents of the third vessel at between 55° C. and 65° C. for between 1 hour and 6 hours, preferably 2 hours, and
v. cooling the contents of the third vessel to between 10° C. and 30° C., wherein the contents of the third vessel comprise a compound of formula I.

Often, the ether solvent is THF. Typically, 0.9 equivalents of $LiAlD_4$ or $LiAlH_4$ and $LiAlD_4$ are added to the third vessel in step iii. The $LiAlD_4$ or $LiAlH_4$ and $LiAlD_4$ is typically added to the third vessel as a 2.4 M or 2 M solution in THF. Sometimes, the $LiAlD_4$ or $LiAlH_4$ and $LiAlD_4$ is added to the third vessel as a 2 M solution in THF.

Sometimes, stage 2 of the method comprises a workup comprising the steps of:

vi. adding between 5 and 20 volumes of an aqueous solution of a tartrate salt (such as Rochelle's salts) to a fourth vessel,
vii. adding a composition comprising crude compound of formula I, over at least 15 minutes (such as 15 minutes to 1 hour), preferably at least 30 minutes (such as 30 minutes to 1 hour), to the fourth vessel at between 15° C. and 25° C., and
viii. stirring the contents of the fourth vessel at between 15° C. and 25° C. for at least 30 minutes (such as 30 minutes to 1 hour).

For the avoidance of doubt, the composition comprising crude compound of formula I refers to the contents of the third vessel on completion of step v. of stage 2, described above.

Stage 2 of the method may further comprise the steps of:

ix. allowing an organic fraction to separate from an aqueous fraction, wherein the organic fraction comprises the compound of formula I,
x. removing the aqueous fraction from the fourth vessel,
xi. adding between 5 and 20 volumes of a brine solution to the fourth vessel,
xii. stirring the contents of the fourth vessel at a temperature between 15° C. and 25° C. for at least 5 minutes (such as 5 to 15 minutes),
xiii. removing the organic fraction comprising the compound of formula I as a freebase, xiv. drying the organic fraction using a drying agent, such as a drying agent selected from calcium chloride, magnesium sulphate, and sodium sulphate, xv. filtering the organic fraction, and xvi. concentrating the organic fraction, for example under vacuum such as under a pressure of less than 1 atmosphere.

Isolated compounds of formula I (produced via stage 2) are stable and may be stored as solids at ambient temperature, e.g. at about 20° C., in the air. They may, but need not be, stored under inert conditions, e.g. under nitrogen or argon, or at reduced temperatures, e.g. in a refrigerator or freezer. Sometimes, the compound of formula I is stored in a solvent, for example dissolved in ethanol. Sometimes, the compound of formula I is stored in a solvent for more than 8 hours, typically more than 12 hours.

As described above, the compound of formula I may be in the form of a pharmaceutically acceptable salt. A pharmaceutically acceptable salt may be formed from a compound of formula I by reaction with a suitable acid. Thus, the method may further comprise a stage 3, in which the compound of formula I is reacted with an acidic reagent to produce a pharmaceutically acceptable salt of the compound of formula I. The acidic reagent may be suitable for crystallising a pharmaceutically acceptable salt of the compound of formula I.

For the avoidance of doubt, where a reagent is expressed herein as a number of equivalents, this is with respect to the molar equivalents of the compound of formula III, formula II or formula I for reagents in stage 1, stage 2 or stage 3 respectively.

A method of synthesising a compound of formula I, or a pharmaceutically acceptable salt thereof often comprises stage 1, stage 2 and stage 3, wherein stage 1 comprises:

(i) reacting a compound of formula III with two or more coupling agents to produce an activated compound;

(ii) reacting the activated compound with an amine having the formula $(R^2)_2NH$ to produce a compound of formula II; and (iii) isolating the compound of formula II;

stage 2 comprises reacting the compound of formula II with $LiAlD_4$ or $LiAlH_4$ and $LiAlD_4$; and stage 3 comprises the step of reacting the compound of formula I with an acidic reagent suitable for crystallising a pharmaceutically acceptable salt of the compound of formula I.

Sometimes, a ratio of acidic reagent:compound of formula I of ≥1:1 is used. Often, the ratio of acidic reagent:compound of formula I is 1:1.

Typically, stage 3 of the method is carried out in a suitable solvent. The skilled person is able to assess which solvents are suitable for stage 3. Examples of suitable solvents include ethanol, IPA, iPrOAc and MeCN. Stage 3 is often carried out in ethanol.

Stage 3 of the method of the invention is carried out at a suitable temperature and the skilled person is able to assess which temperatures are suitable for these steps.

Stage 3 of the method often comprises contacting a compound of formula I and an acidic reagent to produce a first composition. Often, the contacting of stage 3 is carried out at temperatures of 70 to 100° C., for example 70 to 90° C. or 70 to 80° C. Sometimes, the contacting of stage 3 is carried out at temperatures of about 75° C.

Often, stage 3 further comprises isolating the pharmaceutically acceptable salt of formula I. The skilled person is aware of techniques in the art suitable for isolation of such a compound. For example, where the compound is dissolved within a suspension, it may be separated from some of the other components of the suspension via filtration, such as hot filtration. The pharmaceutically acceptable salt of formula I may precipitate from the filtrate. The skilled person is aware of methods to encourage precipitation of a compound from a solution, such as cooling the solution, concentrating the solution and/or adding into the solution a crystalline form of the compound to encourage nucleation and the growth of further crystals of the compound from the solution (i.e. seeding). The pharmaceutically acceptable salt of formula I may be recrystallized. The skilled person is aware of techniques that are suitable for recrystallisation of a pharmaceutically acceptable salt of formula I. The examples of recrystallisation techniques described with respect to recrystallisation of a compound of formula II apply mutatis mutandis to recrystallisation of a pharmaceutically acceptable salt of formula I.

Stage 3 of the method may comprise the steps of:

i. adding to a fifth vessel at least one equivalent of an acidic reagent suitable for crystallising a pharmaceutically acceptable salt of a compound of formula I, ii. dissolving a compound of formula I as a freebase in between 5 and 20 volumes of a solvent such as a solvent selected from ethanol, IPA, iPrOAc and MeCN and adding the solution to the fifth reaction vessel, iii. stirring the contents of the fifth vessel at a temperature of above 72° C. (such as 72 to 90° C.), iv. filtering the contents of the fifth vessel, v. adding the filtrate to a sixth vessel and cooling the contents to a temperature of 67° C. to 73° C., vi. optionally seeding the sixth vessel with a crystalline form of the pharmaceutically acceptable salt of the compound of formula I, vii. stirring the contents of the sixth vessel at a temperature of 67° C. to 73° C. for at least 30 minutes (such as 30 minutes to 1 hour), viii. cooling the contents of the sixth vessel to a temperature of −5° C. to 5° C. at a rate of 2 to 8° C. per hour, and ix. filtering the contents of the sixth vessel to produce a filter cake comprising a pharmaceutically acceptable salt of the compound of formula I.

Often, the solvent of step ii. is ethanol. Often, the rate of cooling in step viii. is 5° C. per hour.

As described above, the pharmaceutically acceptable salt often comprises a compound of formula I and a suitable acid. The acids listed above as suitable components of the pharmaceutically acceptable salts of the invention apply mutatis mutandis to the acidic reagents of stage 3 of the method Often, the acidic reagent is any one selected from fumaric acid, tartaric acid, citric acid and hydrochloric acid, such as fumaric acid.

Examples of preferred psychedelic tryptamines which can be prepared by the synthetic methods described above include those listed in Table 1. $R^1$ and $R^2$ of the compounds disclosed herein may be any of the combinations depicted in Table 1. Also shown in Table 1 are the molecular weights of preferred drug substances comprising a compound of formula I and mixtures of protio and deutero analogues thereof.

TABLE 1

Examples of psychedelic tryptamines which can be prepared by synthetic methods disclosed herein

| Compound | $R^1$ | $R^2$ | Preferred m/w range of alpha deuterated substances in Daltons (as freebase) |
|---|---|---|---|
| 4-OAc-DET | 4-OC(O)CH$_3$ | ethyl | 274.5-276.4 |
| 4-OAc-DIPT | 4-OC(O)CH$_3$ | iso-propyl | 302.5-304.4 |
| 4-OAc-DMT | 4-OC(O)CH$_3$ | methyl | 246.4-248.3 |
| 5-OAc-DMT | 5-OC(O)CH$_3$ | methyl | 246.4-248.3 |
| 4-OAc-DPT | 4-OC(O)CH$_3$ | n-propyl | 302.5-304.4 |
| 4-OAc-MET | 4-OC(O)CH$_3$ | methyl, ethyl | 260.4-262.3 |
| 4-OAc-MIPT | 4-OC(O)CH$_3$ | methyl, iso-propyl | 274.5-276.4 |
| 2-Me-DET | 2-Me | ethyl | 230.5-232.4 |
| 5-MeO-DIPT | 5-OCH$_3$ | iso-propyl | 274.5-276.4 |
| 5-MeO-DMT | 5-OCH$_3$ | methyl | 218.4-220.3 |
| 4-MeO-MIPT | 5-OCH$_3$ | methyl, iso-propyl | 246.5-248.4 |
| 5-MeO-MIPT | 5-COH$_3$ | methyl, iso-propyl | 246.5-248.4 |

The synthetic method disclosed herein is particularly useful for producing therapeutic deuterated substituted dialkyl tryptamines, as the method employs significantly less LiAlD$_4$ than other syntheses known in the art since the method substitutes deuterium at the alpha position but not the beta position. LiAlD$_4$ is among the most expensive and difficult to manufacture reagents in this synthesis. Moreover, optimised methods disclosed herein reduce LiAlD$_4$ or LiAlH$_4$ and LiAlD$_4$ requirements, for example from 2 equivalents to 0.9 equivalents which increases economic efficiency in manufacturing deuterated compounds of formula I. In view of this, compounds of formula I are cheaper to make, via the synthetic method disclosed herein, than known deuterated analogues which are typically deuterated at both the alpha and beta position.

The synthetic method disclosed herein is efficient; compounds of formula I may be produced with an overall yield of between 50% and 100%, such as between 60% and 100% or between 65% and 100%.

Also disclosed herein is a kit suitable for preparing a compound of formula I wherein the kit comprises:
(A) a compound of formula III,
(B) two or more coupling agents,
(C) an amine having the formula (R$^2$)$_2$NH,
(D) LiAlD$_4$ or LiAlH$_4$ and LiAlD$_4$, and
(E) an acidic reagent suitable for the production of a pharmaceutically acceptable salt of the compound of formula I;
wherein the compounds of formulae I and III are as defined in relation to the synthetic method disclosed herein.

For the avoidance of doubt, disclosures related to the compounds of formulae I and III, or pharmaceutically acceptable salts thereof, the two or more coupling agents, the amine of formula (R$^2$)$_2$NH, LiAlD$_4$ or LiAlH$_4$ and LiAlD$_4$, and the acidic reagent of the synthetic method disclosed herein apply mutatis mutandis to the kit. For example, R$^2$ of the amine of formula (R$^2$)$_2$NH (and thus compound of formula I or pharmaceutically acceptable salt thereof) may be methyl; R$^1$ of formulae I and III may be methoxy or acetoxy; and/or n may be 1 and R$^1$ may be at the 4- or 5-position; the two or more coupling agents may comprise a carbodiimide coupling agent and an additive coupling agent; the ratio of LiAlD$_4$ or LiAlH$_4$ and LiAlD$_4$: compound of formula III may be 0.8:1 to 1:1; and/or the acidic reagent may be fumaric acid.

As described above, the inventors have observed a quantifiable relationship between the extent of deuteration and the effect on potentiation of the metabolic half-life of the parent compound. Viewed from a third aspect, there is provided a composition comprising at least a first and a second compound, or pharmaceutically acceptable salts thereof, wherein the first compound is selected from the compounds defined in the first or second aspects and the second compound is an undeuterated analogue of the first compound.

The first compound comprises 1 or 2 deuterium atoms at the α-position but, other than the presence of the 1 or 2 deuterium atoms, is identical to the second (undeuterated, i.e. protio) compound.

Often, the composition comprises 2%, 5%, 10%, 15%, 20%, 25%, 30%, 50%, 60%, 75%, 90%, 95%, 96% or 98% or more by weight of the first compound. In some embodiments, the composition comprises between 2% and 90%, 2% and 95%, 2% and 96%, 2% and 97%, 2% and 98%, for example between 5% and 90%, 5% and 95%, 5% and 96%, 5% and 97%, 5% and 98%; 10% and 90%, 10% and 95%, 10% and 96%, 10% and 97%, 10% and 98%; 15% and 90%, 15% and 95%, 15% and 96%, 15% and 97%, 15% and 98%; 20% and 90%, 20% and 95%, 20% and 96%, 20% and 97%, 20% and 98%; 25% and 90%, 25% and 95%, 25% and 96%, 25% and 97%, 25% and 98%; 30% and 90%, 30% and 95%, 30% and 96%, 30% and 97%, 30% and 98%; 50% and 90%, 50% and 95%, 50% and 96%, 50% and 97%, 50% and 98%; 60% and 90%, 60% and 95%, 60% and 96%, 60% and 97%, 60% and 98%; or 75% and 90%, 75% and 95%, 75% and 96%, 75% and 97%, 75% and 98%, by weight of the first compound.

The composition may comprise from 2% to 98% by weight of the second compound, and preferably comprises from 5% to 95% by weight of the second compound. Preferred compositions comprise from 10% to 90% by weight of the second compound, or from 15% to 85% by weight of the second compound, or from 20% to 80% by weight of the second compound, or from 25% to 75% by weight of the second compound, or from 30% to 70% by weight of the second compound, or from 40% to 60% by weight of the second compound.

The composition preferably comprises from 5% to 95% by weight of the first compound.

In some embodiments, the composition comprises a first, second and third compound, wherein the first compound is selected from the compounds defined in the first or second aspects with the proviso that $^xH$ is protium, the second compound is an undeuterated analogue of the first compound and the third compound is a deuterated analogue of the first compound, which differs from the first compound only in that $^xH$ is deuterium rather than protium.

Typically, the composition comprises 2% or more by weight of the first or third compound. In some embodiments, the composition comprises 2% or more by weight of the first compound. In some embodiments, the composition comprises 2% or more by weight of the first compound and 2% or more by weight of the third compound.

It will be understood that, wherever a composition comprises 2% or more by weight of a first or third compound, that such compositions may comprise up to 95%, up to 96%, up to 97% or up to 98% by weight of the first or third compound.

In some embodiments, the first compound comprises up to 50% by weight of the total composition. It will be understood that, in such embodiments, such compositions may comprise 2% or more by weight, for example 5% or more, 10% or more, 15% or more, 20% or more, 25% or more or 30% or more, based on the total composition, of the first compound.

According to specific embodiments, the composition consists essentially of at least a first and a second compound, or pharmaceutically acceptable salts thereof, wherein the first compound is selected from the compounds defined in the first or second aspects and the second compound is an undeuterated analogue of the first compound. By the composition consisting essentially of at least a first and a second compound is meant that the composition may comprise additional components (other than the at least a first and a second compound) but that the presence of these additional components will not materially affect the essential characteristics of the composition. In particular, compositions consisting essentially of at least a first and a second compound will not comprise material amounts of other pharmaceutically active substances (i.e. material amounts of other drug substances).

Figure 3:
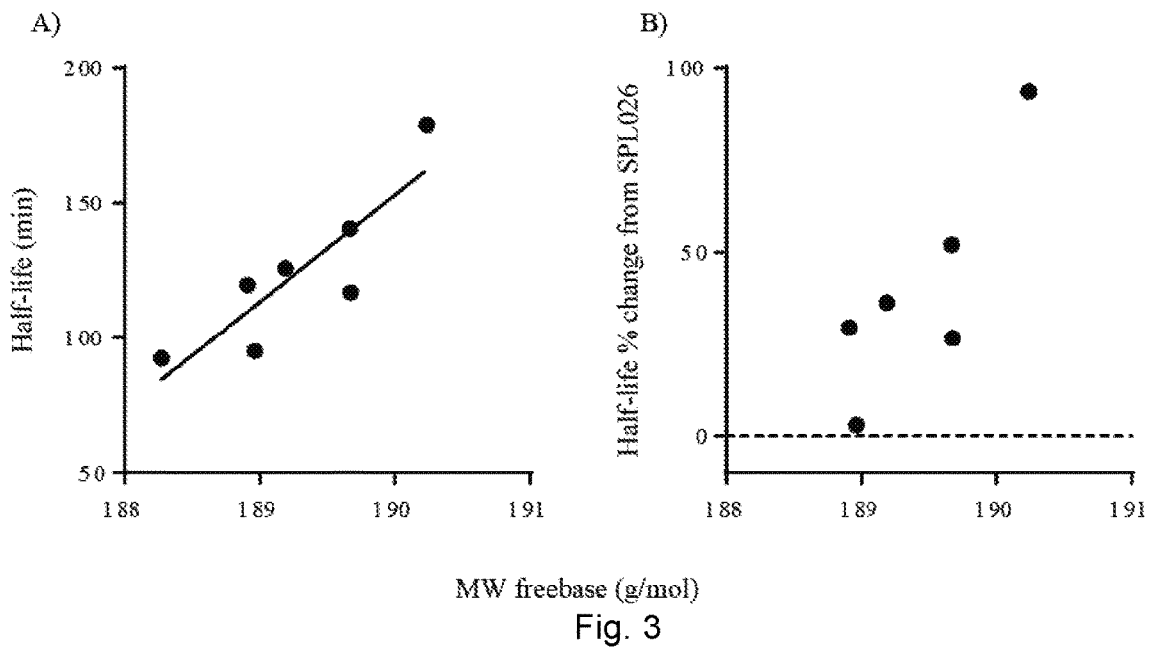
FIG. 3 plots calculated in vitro half-life for DMT and 6 deuterated-containing compositions described in Example 4. A) Linear regression analysis. The r2 value for half-life is 0.754; where the slope was found to be significantly different to zero, p=0.01. B) Half-life of deuterated analogues as a percent change from (undeuterated) DMT (dashed line).
Figure 4:
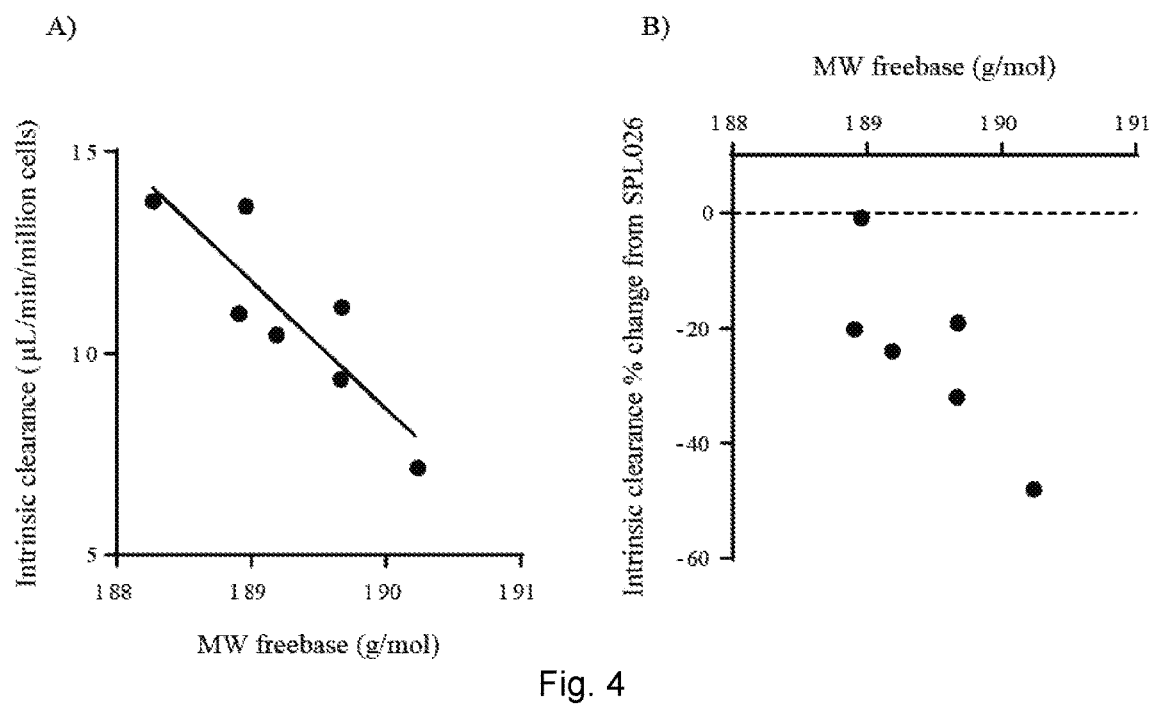
FIG. 4 In vitro intrinsic clearance for DMT and 6 deuterium-containing compositions described in Example 4. A) Linear regression analysis. The $r^2$ value for intrinsic clearance is 0.7648; where the slope was found to be significantly different to zero, p=0.01. B) Intrinsic clearance of deuterated analogues as a percent change from (undeuterated) DMT (dashed line).

As detailed in the Examples section, and related FIGS. 3 and 4, the inventors have demonstrated that increasing deuterium enrichment at the α-carbon of N,N-dimethyltryptamine increases metabolic stability, leading to a decrease in clearance and longer half-life. A linear relationship exists between molecular weight and half-life, in particular when the input reducing agent for production of the deuterium-enriched N,N-dimethyltryptamine-containing compositions of this invention comprise $LiAlH_4$ and $LiAlD_4$ with ratio between about 1-2.5 and about 2.5:1.

According to particular embodiments, the composition of the third aspect comprises at least a first and a second compound, or pharmaceutically acceptable salts thereof, wherein the first compound is selected from the compounds defined in the first or second aspects, wherein $R^1$ and $R^2$ are as defined in Table 1, and the second compound is an undeuterated analogue of the first compound. In some embodiments, the mean molecular weight of the composition is as defined in Table 1.

In some embodiments, the composition comprises a first, second and third compound, wherein the first compound is selected from the compounds defined in the first or second aspects, wherein $R^1$ and $R^2$ are as defined in Table 1, with the proviso that $^xH$ is protium, the second compound is an undeuterated analogue of the first compound and the third compound is a deuterated analogue of the first compound, which differs from the first compound only in that $^xH$ is deuterium rather than protium. In some embodiments, the mean molecular weight of the composition is as defined in Table 1.

In some embodiments, the composition of the third aspect consists essentially of the first, second and optionally third compounds. As used herein, mean molecular weight means the weighted average of molecular weights of the first, second and optionally third compound, as measured by an appropriate mass spectroscopic technique, for example LC-MS SIM (selected-ion monitoring), ignoring any weight contribution by formation of pharmaceutically acceptable salts, where applicable. In some embodiments, the mean molecular weight is the weighted average.

It will be understood that providing compositions with such specific mean molecular weights can be achieved by those skilled in the art through the teachings herein, in particular by adjusting the relative proportions of lithium aluminium hydride and lithium aluminium deuteride in the reductions described herein.

By reciting that the composition consists essentially of the first, second and optionally third compound means that the composition may comprise additional components to these but that the presence of such additional components will not materially affect the essential characteristics of the composition. In particular, the composition will not comprise material quantities of other pharmaceutically active compounds, including other compounds of formula I and/or their protio analogues.

In other words, and alternatively put, the compositions according to these specific embodiments constitute a drug substance comprising a biologically active ingredient consisting essentially of a mixture of the first, second and optionally third compound, wherein the drug substance is optionally in the form of a pharmaceutically acceptable salt.

It will be understood that the compositions according to these specific embodiments comprise the first and optionally third compound in amounts greater than found in isotopically unenriched protio analogues. It will also be understood that the greater the proportion of the first and optionally third compounds in these specific embodiments, the higher the mean molecular weight of the composition.

Viewed from a fourth aspect, there is provided a pharmaceutical composition comprising a compound as defined in the first aspect or a compound of the second aspect, or pharmaceutically acceptable salts thereof, or the composition of the third aspect in combination with a pharmaceutically acceptable excipient.

The pharmaceutical composition of the invention may comprise one or more pharmaceutically acceptable excipients. Suitable pharmaceutical compositions can be prepared by the skilled person, with examples of pharmaceutically acceptable excipients including but not being limited to those described in Gennaro et. al., Remmington: *The Science and Practice of Pharmacy*, $20^{th}$ Edition, Lippincott, Williams and Wilkins, 2000 (specifically part 5: pharmaceutical manufacturing). Suitable excipients are also described in the Handbook of Pharmaceutical Excipients, $2^{nd}$ Edition; Editors A. Wade and P. J. Weller, American Pharmaceutical Association, Washington, The Pharmaceutical Press, London, 1994. M. F. Powell, T. Nguyen and L. Baloian provide a review of excipients suitable for parenteral administration (administration other than by the mouth or alimentary canal) in PDA J. Pharm. Sci. Technol., 52, 238-311 (1998). All soluble excipients listed in this review article are suitable excipients for use in the fourth aspect of the invention. Compositions include those suitable for oral, nasal, topical (including buccal, sublingual and transdermal), parenteral (including subcutaneous, intravenous and intramuscular) or rectal administration.

The pharmaceutical compositions of the invention, may be compressed into solid dosage units, such as tablets, or be processed into capsules or suppositories. By means of pharmaceutically suitable liquids the compounds can also be prepared in the form of a solution, suspension, emulsion, or as a spray. For making dosage units, including tablets, the use of conventional additives such as fillers, colorants, polymeric binders and the like is contemplated. In general, any pharmaceutically acceptable additive can be used.

Suitable fillers with which the pharmaceutical compositions can be prepared and administered include lactose, starch, cellulose and derivatives thereof, and the like, or mixtures thereof used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention also provides a pharmaceutical composition of the invention, in combination with packaging material suitable for the composition, the packaging material including instructions for the use of the pharmaceutical composition.

As described above, the compounds and compositions of the invention have uses in the treatment of psychiatric or neurological disorders. Thus, viewed from a fifth aspect, there is provided the composition of the third or fourth aspects for use in therapy.

In some embodiments, the therapy is psychedelic-assisted psychotherapy, i.e. the therapy is treatment of a mental disorder by psychological means, which are enhanced by one or more protocols in which a patient is subjected to a psychedelic experience induced by administration of the compound or composition.

Viewed from a sixth aspect, there is provided a compound as defined in the first or second aspect, a pharmaceutically acceptable salt thereof, or composition of the third or fourth aspects for use in a method of treating a psychiatric or neurological disorder in a patient.

In another aspect, the invention provides use of a compound defined in the first or second aspects, pharmaceutically acceptable salts thereof or a composition of the third or fourth aspects for the manufacture of a medicament. In some embodiments, the medicament is for use in a method of treating a psychiatric or neurological disorder in a patient.

In some embodiments, the psychiatric or neurological disorder is selected from (i) an obsessive compulsive disorder, (ii) a depressive disorder, (iii) a schizophrenia disorder, (iv) a schizotypal disorder, (v) an anxiety disorder, (vi) substance abuse, and (vii) an avolition disorder. Often, the psychiatric or neurological disorder is selected from the group consisting of (i) an obsessive compulsive disorder, (ii) a depressive disorder, (iii) an anxiety disorder, (iv) substance abuse, and (v) an avolition disorder.

In some embodiments, the disorder is selected from the group consisting of major depressive disorder, treatment resistant major depressive disorder, post-partum depression, an obsessive compulsive disorder and an eating disorder such as a compulsive eating disorder.

In some embodiments, the psychiatric or neurological disorder is major depressive disorder. In some embodiments, the psychiatric or neurological disorder is treatment resistant depression.

As described above, the compounds of the invention have improved oral bioavailability as their metabolism by monoamine oxidase enzymes in the gastrointestinal tract is slower than their α-diprotic analogues. Thus, in some embodiments, the therapy or method of treatment comprises oral administration of the compound, pharmaceutically acceptable salt thereof or composition.

Viewed from a seventh aspect, there is provided a method of treatment comprising administering to a patient in need thereof a compound as defined in the first or second aspect, a pharmaceutically acceptable salt thereof or composition of the third or fourth aspects.

In some embodiments, the method of treatment is psychedelic-assisted psychotherapy, i.e. the method of treatment is treatment of a mental disorder by psychological means, which are enhanced by one or more protocols in which a patient is subjected to a psychedelic experience induced by administration of the compound or composition.

In some embodiments, the method of treatment is a method of treating a psychiatric or neurological disorder. For the avoidance of doubt, embodiments related to the method of treatment, of the fifth or sixth aspects of the invention apply mutatis mutandis to the seventh aspect. For example, the disorder may be selected from the group consisting of (i) an obsessive compulsive disorder, (ii) a depressive disorder, (iii) an anxiety disorder, (iv) substance abuse, and (v) an avolition disorder; and/or the method of treatment may comprise oral administration of the compound or composition.

In order to treat the disorder, an effective amount of the compound, pharmaceutically acceptable salt or composition is administered, i.e. an amount that is sufficient to reduce or halt the rate of progression of the disorder, or to ameliorate or cure the disorder and thus produce the desired therapeutic or inhibitory effect.

As described above, the compounds of the invention have improved oral bioavailability. Accordingly, viewed from an eighth aspect, there is provided an oral dosage form comprising a compound as defined in the first or second aspect, a pharmaceutically acceptable salt thereof or a composition of the third or fourth aspects. By "oral dosage form" is meant a particular configuration (such as a tablet or capsule, for example) comprising a particular dose of the compound or composition, wherein the configuration is suitable for oral administration. The oral dosage form may be a solid dosage form, such as a tablet, capsule, sachet, powder or granule, or a liquid or semi-solid oral dosage form such as a syrup, solution, ampoule, or dispersion. Typically, the oral dosage form is a solid dosage form, often a tablet or a capsule.

Each and every reference referred to herein is hereby incorporated by reference in its entirety, as if the entire content of each reference was set forth herein in its entirety.

The invention may be further understood with reference to the following non-limiting clauses and examples following thereafter:

1. A compound of formula I. or a pharmaceutically acceptable salt thereof,

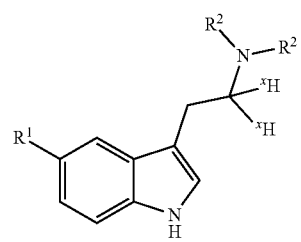

I wherein at least one $^xH$ is deuterium, $R^1$ is selected from $R^3$, $OR^3$, $O(CO)R^3$, F, Cl, Br or I, and each $R^2$ and $R^3$ is independently selected from $C_1$-$C_4$ alkyl.

2. The compound of clause 1 wherein $R^1$ is $OR^3$, preferably OMe.

3. The compound of clause 1 or 2 wherein each $R^2$ is methyl.

4. The compound of any of clauses 1 to 3 wherein both $^xH$ are deuterium.

5. A method of synthesising a compound of formula I, or a pharmaceutically acceptable salt thereof, comprising two stages wherein stage 1 comprises the step of reacting a compound of formula III with a combination of two or more coupling agents followed by an amine having the formula $(R^2)_2NH$, and stage 2 comprises the step of reducing the compound of formula II with $LiAl^xH_4$,

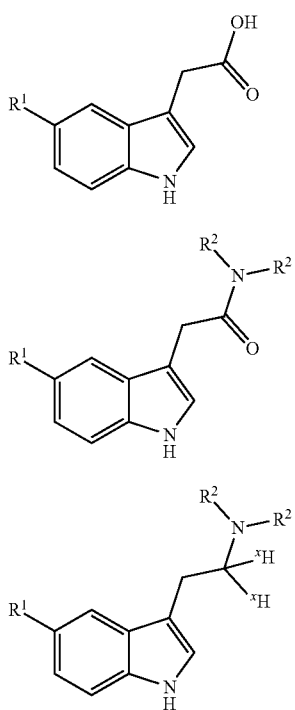

wherein LiAl$^x$H$_4$ is LiAlD$_4$ and optionally comprising between 0.1 and 99.9% LiAlH$_4$, each R$^1$ is independently selected from R$^3$, OR$^3$, O(CO)R$^3$, F, Cl, Br or I, and each R$^2$ and R$^3$ is independently selected from C$_1$-C$_4$ alkyl.

6. The method of clause 5 wherein the compound of formula I is a pharmaceutically acceptable salt, said method consisting essentially of three stages wherein stage 1 comprises the steps of:
 i. reacting the compound of formula III with a combination of two or more coupling agents,
 ii. reacting the resulting intermediate with an amine having the formula (R$^2$)$_2$NH; and
 iii. isolating the compound of formula II;
stage 2 comprises the step of reducing the compound of formula II with LiAl$^x$H$_4$; and
stage 3 comprises the step of reacting the compound of formula I with an acidic reagent suitable for crystallising a pharmaceutically acceptable salt of the compound of formula I.

7. The method of clause 5 or 6 wherein stage 1 comprises the steps of
 iv. adding to a first vessel 1 g or more of a compound of formula III and between 1 and 1.5 equivalents of an additive coupling agent,
 v. adding to the first vessel between 5 and 20 volumes of a first solvent selected from DCM, Acetone, IPA, $^i$PrOAc, TBME, 2-MeTHF and EtOAc,
 vi. adding to the first vessel between 1 and 1.5 equivalents of a carbodiimide coupling agent,
 vii. stirring the contents of the first vessel for at least 30 minutes, preferably at least 1 hour, at between 10° C. and 30° C.,
 viii. adding to the first vessel between 1 and 2 equivalents of an amine having the formula (R$^2$)$_2$NH, wherein the amine is preferably dissolved in an ether solvent,
 ix. further stirring the contents of the first vessel for at least 30 minutes, preferably at least 1 hour, at between 10° C. and 30° C.,
 x. adding to the first vessel between 2 and 10 volumes of an aqueous basic solution, preferably 10% potassium carbonate,
 xi. further stirring the contents of the first vessel for at least 1 minute, preferably at least 5 minutes, at between 10° C. and 30° C.,
 xii. allowing an organic fraction to separate from an aqueous fraction, wherein the organic fraction comprises the compound of formula II, and
 xiii. removing the organic fraction comprising the compound of formula II,
wherein steps iv. to xiii. are carried out within a single 8 hour period.

8. The method of any of clauses 5 to 7 wherein the two or more coupling agents comprises EDC, preferably as the HCl salt.

9. The method of any of clauses 5 to 8 wherein the two or more coupling agents comprises an additive coupling agent selected from HOBt, HOOBt, HOSu, HOAt, Ethyl 2-cyano-2-(hydroximino)acetate and DMAP.

10. The method of any of clauses 5 to 9 wherein the two or more coupling agents comprise the carbodiimide EDC.HCl, and the additive coupling agent HOBt.

11. The method of any of clauses 5 to 10 wherein the reaction in stage 1 is carried out in DCM as a solvent.

12. The method of any of clauses 5 to 11 wherein the amine is 2 M dimethylamine in THF.

13. The method of any of clauses 5 to 12 wherein stage 1 further comprises the steps of:
 xiv. drying the organic fraction with a drying agent selected from calcium chloride, magnesium sulphate, and sodium sulphate,
 xv. filtering the organic fraction,
 xvi. concentrating the organic fraction under a pressure of less than 1 atmosphere,
 xvii. adding the concentrated organic fraction to a second vessel,
 xviii. adding between 2 and 10 volumes of a second solvent to the second vessel, wherein the second solvent is selected from IPA, EtOAc, IPrOAc, MeCN, TBME, THF, 2-MeTHF and toluene,
 xix. stirring the contents of the second vessel for at least 1 hour, preferably at least 2 hours, between 45° C. and 55° C.,
 xx. cooling the contents of the second vessel to between 15° C. and 25° C.,
 xxi. filtering contents of the second vessel to obtain a filtrate, wherein the filtrate comprises the compound of formula II, and
 xxii. drying the filtrate.

14. The method of clause 13 wherein the second solvent is selected from TBME and IPA.

15. The method of any of clauses 5 to 14 wherein stage 2 comprises the steps of
 xxiii. adding to a third vessel 1 g or more of a compound of formula II,
 xxiv. adding to the third vessel between 5 and 20 volumes of an ether solvent,
 xxv. adding to the third vessel, dropwise over at least 15 minutes, a solution of between 0.8 and 1 equivalents of LiAl$^x$H$_4$ in an ether solvent, preferably 2 M dissolved in THF, whilst maintaining the third vessel at a temperature of between −5° C. and 65° C., xxvi. stirring the contents of the third vessel at between 55° C. and 65° C. for between 1 hour and 6 hours, preferably 2 hours, and xxvii. cooling the contents of the third vessel to between 10° C. and 30° C., wherein the contents of the third vessel comprise a compound of formula I.

16. The method of any of clauses 5 to 15 wherein stage 2 comprises a workup comprising the steps of:

xxviii. adding between 5 and 20 volumes of an aqueous solution of a tartrate salt to a fourth vessel, xxix. adding a composition comprising crude compound of Formula III, over at least 15 minutes, preferably at least 30 minutes, to the fourth vessel at between 15° C. and 25° C., and xxx. stirring the contents of the fourth vessel at between 15° C. and 25° C. for at least 30 minutes.

17. The method of clause 16 wherein stage 2 further comprises the steps of xxxi. allowing an organic fraction to separate from an aqueous fraction, wherein the organic fraction comprises the compound of formula I, xxxii. removing the aqueous fraction from the fourth vessel, xxxiii. adding between 5 and 20 volumes of a brine solution to the fourth vessel, xxxiv. stirring the contents of the fourth vessel at a temperature between 15° C. and 25° C. for at least 5 minutes, xxxv. removing the organic fraction comprising the compound of formula I as a freebase, xxxvi. drying the organic fraction using a drying agent selected from calcium chloride, magnesium sulphate, and sodium sulphate, xxxvii. filtering the organic fraction, and xxxviii. concentrating the organic fraction under a pressure of less than 1 atmosphere.

18. The method of any of clauses 5 to 17 wherein stage 3 comprises the steps of xxxix. adding to a fifth vessel at least one equivalent of an acidic reagent suitable for crystallising a pharmaceutically acceptable salt of a compound of formula I, xl. dissolving 1 g or more of a compound of formula I as a freebase in between 5 and 20 equivalents of a solvent selected from ethanol, IPA, $^i$PrOAc and MeCN and adding the solution to the fifth reaction vessel, xli. stirring the contents of the fifth vessel at a temperature above 72° C., xlii. filtering the contents of the fifth vessel, xliii. adding the filtrate to a sixth vessel and cooling the contents to a temperature of 67° C. to 73° C., xliv. optionally seeding the sixth vessel with a crystalline form of the pharmaceutically acceptable salt of the compound of formula I, xlv. stirring the contents of the sixth vessel at a temperature of 67° C. to 73° C. for at least 30 minutes, xlvi. cooling the contents of the sixth vessel to a temperature of −5° C. to 5° C. at a rate of 2 to 8° C. per hour, and xlvii. filtering the contents of the sixth vessel to produce a filter cake comprising a pharmaceutically acceptable salt of the compound of formula I.

19. The method of any of clauses 5 to 18 wherein the compound of formula I, or a pharmaceutically acceptable salt thereof, is produced at a purity of greater than 99% by HPLC.

20. The compound of any of clauses 1 to 4 obtainable by a method of any one of clauses 5 to 19.

21. The compound of any of clauses 1 to 4 and 20 for use in psychedelic-assisted psychotherapy.

22. The compound of any of clauses 1 to 4 for use in treating a psychiatric or psychocognitive disorder selected from (i) an obsessive compulsive disorder, (ii) a depressive disorder, (iii) a schizophrenia disorder, (iv) a schizotypal disorder, (v) an anxiety disorder, (vi) substance abuse, and (vii) an avolition disorder.

23. A kit for synthesising a compound of formula I wherein the kit comprises:

a. a compound of formula III, b. two or more coupling agents, c. an amine having the formula $(R^2)_2NH$, d. LiAl$^x$H$_4$, and optionally e. an acidic reagent suitable for crystallising a pharmaceutically acceptable salt of the compound of formula I

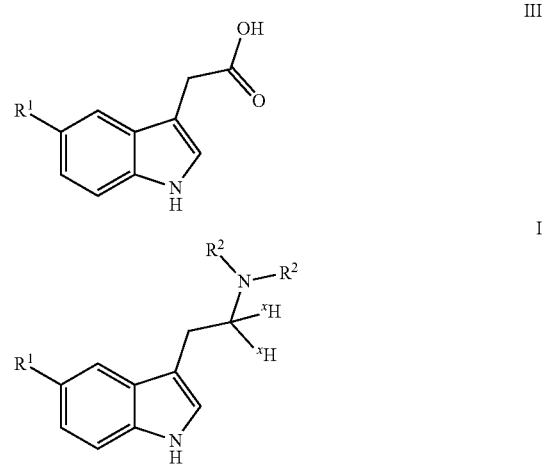

wherein LiAl$^x$H$_4$ is LiAlH$_4$, LiAlD$_4$ or a mixture thereof, each $R^1$ is independently selected from $R^3$, $OR^3$, $O(CO)R^3$, F, Cl, Br or I, and each $R^2$ and $R^3$ is independently selected from $C_1$-$C_4$ alkyl.

24. An oral dosage form comprising a compound of any one of clauses 1 to 4 and 21 to 24.

25. The compound, method, kit, or oral dosage form of any previous claim wherein the compound of formula I is selected from α-deutero-5-methoxydimethyltryptamine, α,α-dideutero-5-methoxydimethyttryptamine or a mixture thereof.

26. A method of synthesising a compound of formula III, or a pharmaceutically acceptable salt thereof, comprising two stages wherein stage 1 comprises the step of reacting a compound of formula I with a combination of two or more coupling agents followed by an amine having the formula $(R^2)_2NH$, and stage 2 comprises the step of reducing the compound of formula II with LiAl$^x$H$_4$,

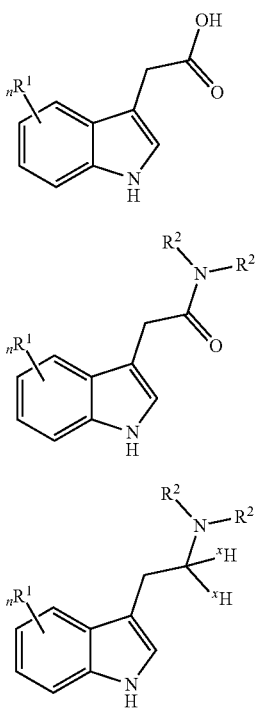

wherein each $^xH$ is independently selected from protium and deuterium,
n is selected from 0, 1, 2, 3 or 4,
each $R^1$ is independently selected from $R^3$, —$OR^3$, —$O(CO)R^3$, F, Cl, Br or I, and
each $R^2$ and $R^3$ is independently selected from $C_1$-$C_4$ alkyl.

27. The method of clause 26 wherein stage 1 further comprises the step of isolating a compound of formula II.

28. The method of clause 26 wherein the compound of formula III is a pharmaceutically acceptable salt, said method consisting essentially of three stages wherein stage 1 comprises the steps of:
  i. reacting the compound of formula I with a combination of two or more coupling agents,
  ii. reacting the resulting intermediate with an amine having the formula $(R^2)_2NH$; and
  iii. isolating the compound of formula II;
  stage 2 comprises the step of reducing the compound of formula II with $LiAl^xH_4$; and
  stage 3 comprises the step of reacting the compound of formula III with an acidic reagent suitable for crystallising a pharmaceutically acceptable salt of the compound of formula III.

29. The method of any of clauses 26 to 28 wherein stage 1 comprises the steps of
  i. adding to a first vessel 1 g or more of a compound of formula I and between 1 and 1.5 equivalents of an additive coupling agent,
  ii. adding to the first vessel between 5 and 20 volumes of a first solvent selected from DCM, Acetone, IPA, $^iPrOAc$, TBME, 2-MeTHF and EtOAc,
  iii. adding to the first vessel between 1 and 1.5 equivalents of a carbodiimide coupling agent,
  iv. stirring the contents of the first vessel for at least 30 minutes, preferably at least 1 hour, at between 10° C. and 30° C.,
  v. adding to the first vessel between 1 and 2 equivalents of an amine having the formula $(R^2)_2NH$, wherein the amine is preferably dissolved in an ether solvent,
  vi. further stirring the contents of the first vessel for at least 30 minutes, preferably at least 1 hour, at between 10° C. and 30° C.,
  vii. adding to the first vessel between 2 and 10 volumes of an aqueous basic solution, preferably 10% potassium carbonate,
  viii. further stirring the contents of the first vessel for at least 1 minute, preferably at least 5 minutes, at between 10° C. and 30° C.,
  ix. allowing an organic fraction to separate from an aqueous fraction, wherein the organic fraction comprises the compound of formula II, and
  x. removing the organic fraction comprising the compound of formula II, wherein steps i. to x. are carried out within a single 8 hour period.

30. The method of any of clauses 26 to 29 wherein the two or more coupling agents comprises EDC, preferably as the HCl salt.

31. The method of any of clauses 26 to 30 wherein the two or more coupling agents comprises an additive coupling agent selected from HOBt, HOOBt, HOSu, HOAt, Ethyl 2-cyano-2-(hydroximino)acetate and DMAP.

32. The method of any of clauses 26 to 31 wherein the two or more coupling agents comprise the carbodiimide EDC.HCl, and the additive coupling agent HOBt.

33. The method of any of clauses 26 to 32 wherein the reaction in stage 1 is carried out in DCM as a solvent.

34. The method of any of clauses 26 to 33 wherein the amine is 2 M dimethylamine in THF.

35. The method of any of clauses 28 to 34 wherein stage 1 further comprises the steps of:
  xi. drying the organic fraction with a drying agent selected from calcium chloride, magnesium sulphate, and sodium sulphate,
  xii. filtering the organic fraction,
  xiii. concentrating the organic fraction under a pressure of less than 1 atmosphere,
  xiv. adding the concentrated organic fraction to a second vessel,
  xv. adding between 2 and 10 volumes of a second solvent to the second vessel, wherein the second solvent is selected from IPA, EtOAc, IPrOAc, MeCN, TBME, THF, 2-MeTHF and toluene,
  xvi. stirring the contents of the second vessel for at least 1 hour, preferably at least 2 hours, between 45° C. and 55° C.,
  xvii. cooling the contents of the second vessel to between 15° C. and 25° C.,
  xviii. filtering contents of the second vessel to obtain a filtrate, wherein the filtrate comprises the compound of formula II, and
  xix. drying the filtrate.

36. The method of clause 35 wherein the second solvent is selected from TBME and IPA.

37. The method of any of clauses 26 to 36 wherein stage 2 comprises the steps of
  i. adding to a third vessel 1 g or more of a compound of formula II,
  ii. adding to the third vessel between 5 and 20 volumes of an ether solvent,
  iii. adding to the third vessel, dropwise over at least 15 minutes, a solution of between 0.8 and 1 equivalents of $LiAl^xH_4$ in an ether solvent, preferably 2 M dissolved in THF, whilst maintaining the third vessel at a temperature of between −5° C. and 65° C., iv. stirring the contents of the third vessel at between 55° C. and 65° C. for between 1 hour and 6 hours, preferably 2 hours, and v. cooling the contents of the third vessel to between 10° C. and 30° C., wherein the contents of the third vessel comprise a compound of formula III.

38. The method of any of clauses 26 to 37 wherein stage 2 comprises a workup comprising the steps of:

vi. adding between 5 and 20 volumes of an aqueous solution of a tartrate salt to a fourth vessel, vii. adding a composition comprising crude compound of formula III, over at least 15 minutes, preferably at least 30 minutes, to the fourth vessel at between 15° C. and 25° C., and viii. stirring the contents of the fourth vessel at between 15° C. and 25° C. for at least 30 minutes.

39. The method of clause 38 wherein stage 2 further comprises the steps of ix. allowing an organic fraction to separate from an aqueous fraction, wherein the organic fraction comprises the compound of formula III, x. removing the aqueous fraction from the fourth vessel, xi. adding between 5 and 20 volumes of a brine solution to the fourth vessel, xii. stirring the contents of the fourth vessel at a temperature between 15° C. and 25° C. for at least 5 minutes, xiii. removing the organic fraction comprising the compound of formula III as a freebase, xiv. drying the organic fraction using a drying agent selected from calcium chloride, magnesium sulphate, and sodium sulphate, xv. filtering the organic fraction, and xvi. concentrating the organic fraction under a pressure of less than 1 atmosphere.

40. The method of any of clauses 26 to 39 wherein stage 3 comprises the steps of i. adding to a fifth vessel at least one equivalent of an acidic reagent suitable for crystallising a pharmaceutically acceptable salt of a compound of formula III, ii. dissolving 1 g or more of a compound of formula III as a freebase in between 5 and 20 equivalents of a solvent selected from ethanol, IPA, $^i$PrOAc and MeCN and adding the solution to the fifth reaction vessel, iii. stirring the contents of the fifth vessel at a temperature above 72° C., iv. filtering the contents of the fifth vessel, v. adding the filtrate to a sixth vessel and cooling the contents to a temperature of 67° C. to 73° C., vi. optionally seeding the sixth vessel with a crystalline form of the pharmaceutically acceptable salt of the compound of formula III, vii. stirring the contents of the sixth vessel at a temperature of 67° C. to 73° C. for at least 30 minutes, viii. cooling the contents of the sixth vessel to a temperature of −5° C. to 5° C. at a rate of 2 to 8° C. per hour, and ix. filtering the contents of the sixth vessel to produce a filter cake comprising a pharmaceutically acceptable salt of the compound of formula III.

41. The method of any of clauses 26 to 40 wherein the compound of formula III is obtainable with an overall yield of 50% or greater.

42. The method of any of clauses 26 to 41 wherein the compound of formula III is produced with an overall yield of 65% or greater.

43. The method of any of clauses 26 to 42 wherein the compound of formula III, or a pharmaceutically acceptable salt thereof, is produced at a purity of greater than 99% by HPLC.

44. A composition comprising a compound of formula III, or a pharmaceutically acceptable salt thereof, at a purity of greater than 99.9% by HPLC.

45. The composition of clause 44 wherein the compound of formula III, or a pharmaceutical salt thereof, is present at a purity of greater than 99.95% by HPLC.

46. The composition of any of clauses 44 or 45 having two or fewer impurity peaks by HPLC, wherein no impurity peak by HPLC is greater than 0.2%.

47. The composition of any of clauses 44 to 46 obtainable by a method of any of clauses 26 to 43.

48. The method of any of clauses 26 to 43 or the composition of any of clauses 44 to 47 wherein n is 0, or n is 1 and $R^1$ is selected from 4-methoxy, 5-methoxy, 4-acetoxy, and 5-acetoxy.

49. The method of any of clauses 26 to 43 or 48 or the composition of any of clauses 44 to 48 wherein each $R^2$ is methyl.

50. The composition of any of clauses 44 to 49 for use in psychedelic-assisted psychotherapy.

51. The composition of any of clauses 44 to 50 for use in treating a psychiatric or psychocognitive disorder selected from (i) an obsessive compulsive disorder, (ii) a depressive disorder, (iii) a schizophrenia disorder, (iv) a schizotypal disorder, (v) an anxiety disorder, (vi) substance abuse, and (vii) an avolition disorder.

52. The composition of any of clauses 44 to 51 wherein the compound of formula III is DMT or 5-MeO-DMT.

53. The composition of any of clauses 44 to 52 wherein the pharmaceutically acceptable salt of the compound of formula III is DMT fumarate, and is preferably crystalline having a pattern A polymorphic form.

54. The composition of any of clauses 44 to 53 for use as an antidepressant.

55. A kit for synthesising a compound of formula III wherein the kit comprises:

b. a compound of formula I, c. two or more coupling agents, d. an amine having the formula $R^{22}NH$, e. LiAl$^x$H$_4$, and f. an acidic reagent suitable for crystallising a pharmaceutically acceptable salt of the compound of formula III

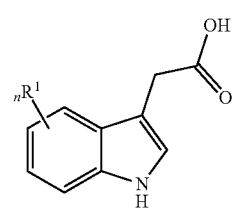

I

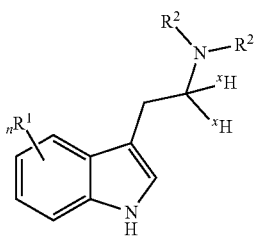

wherein each $^xH$ is independently selected from protium and deuterium,
n is selected from 0, 1, 2, 3 or 4,
each $R^1$ is independently selected from $R^3$, $-OR^3$, $-O(CO)R^3$, F, Cl, Br or I, and
each $R^2$ and $R^3$ is independently selected from $C_1$-$C_4$ alkyl.

EXAMPLES

N,N-DMT 220.9 g (as free base) was prepared as N,N-DMT fumarate, using the chemistry depicted in Scheme 2. An additional 4-6 g of six partially deuterated mixtures were also produced using modified conditions.

Scheme 2
Synthetic route used to prepare dimethyltryptamine fumarate

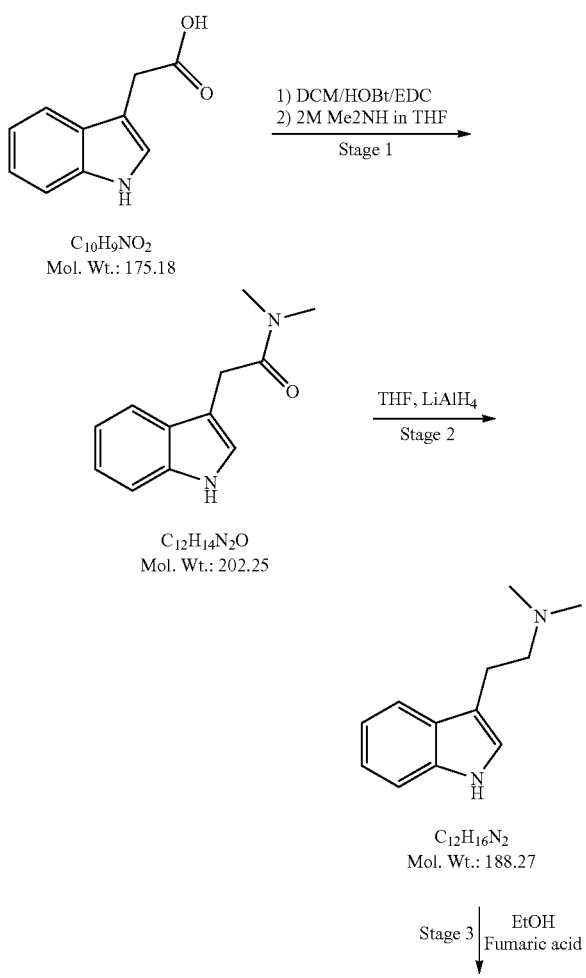

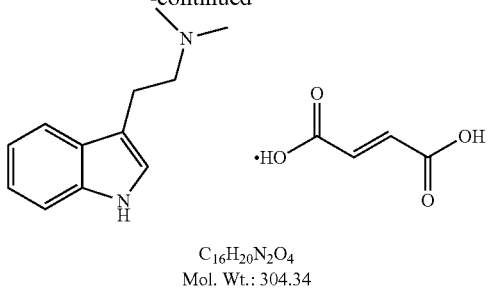

$C_{16}H_{20}N_2O_4$
Mol. Wt.: 304.34

DMT

Stage 1: Coupling of Indole-3-Acetic Acid and Dimethylamine

To a 5 L vessel under $N_2$ was charged indole-3-acetic acid (257.0 g, 1.467 mol), HOBt (~20% wet) (297.3 g, 1.760 mol) and DCM (2313 mL) to give a milky white suspension. EDC.HCl (337.5 g, 1.760 mol) was then charged portionwise over 5 minutes at 16-22° C. The reaction mixture was stirred for 2 hours at ambient temperature before 2 M dimethylamine in THF (1100 mL, 2.200 mol) was charged dropwise over 20 minutes at 20-30° C. The resultant solution was stirred at ambient temperature for 1 hour where HPLC indicated 1.1% indole-3-acetic acid and 98.1% stage 1. The reaction mixture was then charged with 10% $K_2CO_3$ (1285 mL) and stirred for 5 minutes. The layers were separated, and the upper aqueous layer extracted with DCM (643 mL×2). The organic extracts were combined and washed with saturated brine (643 mL). The organic extracts were then dried over $MgSO_4$, filtered and concentrated in vacuo at 45° C. This provided 303.1 g of crude stage 1 as an off-white sticky solid. The crude material was then subjected to a slurry in TBME (2570 mL) at 50° C. for 2 hours before being cooled to ambient temperature, filtered and washed with TBME (514 mL×2). The filter-cake was then dried in vacuo at 50° C. to afford stage 1 266.2 g (yield=90%) as an off-white solid in a purity of 98.5% by HPLC and >95% by NMR.

Stage 2: Preparation of DMT

To a 5 L vessel under $N_2$ was charged stage 1 (272.5 g, 1.347 mol) and THF (1363 mL) to give an off-white suspension. 2.4 M $LiAlH_4$ in THF (505.3 mL, 1.213 mol) was then charged dropwise over 35 minutes at 20-56° C. to give an amber solution. The solution was heated to 60° C. for 2 hours where HPLC indicated stage 1 ND, stage 2 92.5%, Imp 1 2.6%, Imp 2 1.9%. The complete reaction mixture was cooled to ambient temperature and then charged to a solution of 25% Rochelle's salts (aq.) (2725 mL) dropwise over 30 minutes at 20-30° C. The resultant milky white suspension was allowed to stir at 20-25° C. for 1 hour after which the layers were separated and the upper organic layer washed with sat. brine (681 mL). The organic layer was then dried over $MgSO_4$, filtered and concentrated in vacuo at 45° C. The resultant crude oil was subjected to an azeotrope from EtOH (545 mL×2). This provided 234.6 g (yield=92%) of stage 2 in a purity of 95.0% by HPLC and >95% by NMR.

Stage 3a (i)-(iii): Preparation of Seed Crystals of DMT Fumarate (i) Stage 2 (100 mg) was taken up in 8 volumes of isopropyl acetate and warmed to 50° C. before charging fumaric acid (1 equivalent) as a solution in ethanol. The flask was then allowed to mature at 50° C. for 1 hour before cooling to room temperature and stirring overnight, resulting in a white suspension. The solids were isolated by filtration and dried for 4 hours at 50° C. to provide 161 mg of product (>99% yield). Purity by HPLC was determined to be 99.5% and by NMR to be >95%.

(ii) Substitution of isopropyl acetate for isopropyl alcohol in method (i) afforded a white suspension after stirring overnight. The solids were isolated by filtration and dried for 4 hours at 50° C. to provide 168 mg of product (>99% yield). Purity by HPLC was determined to be 99.8% and by NMR to be >95%.

Substitution of isopropyl acetate for tetrahydrofuran in method (i) afforded a white suspension after stirring overnight. The solids were isolated by filtration and dried for 4 hours at 50° C. to provide 161 mg of product (>99% yield). Purity by HPLC was determined to be 99.4% and by NMR to be >95%.

Analysis by x-ray powder diffraction, showed the products of each of methods 9i) to (iii) to be the same, which was labelled Pattern A.

Stage 3b: Preparation of DMT Fumarate

To a 5 L flange flask under $N_2$ was charged fumaric acid (152.7 g, 1.315 mol) and Stage 2 (248.2 g, 1.315 mol) as a solution in ethanol (2928 mL). The mixture was heated to 75° C. to give a dark brown solution. The solution was polish filtered into a preheated (80° C.) 5 L jacketed vessel. The solution was then cooled to 70° C. and seeded with Pattern A (0.1 wt %), the seed was allowed to mature for 30 minutes before cooling to 0° C. at a rate of 5° C./hour. After stirring for an additional 4 hours at 0° C., the batch was filtered and washed with cold ethanol (496 mL×2) and then dried at 50° C. overnight. This provided 312.4 g (yield=78%) of Stage 3 in a purity of 99.9% by HPLC and >95% by NMR. XRPD: Pattern A.

5MeO-DMT

Stage 1: Coupling of 5-methoxyindole-3-acetic Acid and Dimethylamine

To a 100 mL 3-neck flask under $N_2$ was charged 5-methoxyindole-3-acetic acid (3.978 g, 19.385 mmol), HOBt (~20% wet) (3.927 g, 23.261 mmol) and DCM (40 mL). EDC.HCl (4.459 g, 23.261 mmol) was then charged in portions over 15 minutes at <30° C. The reaction mixture was stirred at ambient temperature for 1 hour before being charged with 2 M dimethylamine (14.54 mL, 29.078 mmol) dropwise over 15 minutes at <25° C. After stirring for 1 hour HPLC indicated no starting material (SM, i.e. 5-methoxyindole-3-acetic acid) remained. The reaction mixture was then charged with 10% $K_2CO_3$ (20 mL), stirred for 5 minutes then allowed to separate. The lower aqueous layer was removed and back extracted with DCM (10 mL×2). The organic extracts were combined, washed with saturated brine (10 mL) then dried over $MgSO_4$ and filtered. The filtrate was concentrated in vacuo at 45° C. to provide 3.898 g active (yield=87%) of product in a purity of 95.7% by HPLC.

Stage 2: Preparation of 5MeO-DMT

To a 100 mL 3-neck flask under $N_2$ was charged stage 1 methoxy derivative (3.85 g, 16.586 mmol) and THF (19.25 mL). 2.4 M $LiAlH_4$ in THF (6.22 mL, 14.927 mmol) was then charged dropwise over 30 minutes at <40° C. The reaction mixture was heated to 60° C. for 1 hour where HPLC indicated 0.1% SM (stage 1 methoxy derivative) remained. The reaction mixture was then cooled to ambient temperature and quenched into 25% Rochelle's salts (38.5 mL) dropwise over 30 minutes at <30° C. The resultant suspension was stirred for 1 hour before being allowed to separate. The lower aqueous layer was then removed, and the upper organic layer washed with saturated brine (9.6 mL). The organics were then dried over $MgSO_4$, filtered and concentrated in vacuo before being subjected to an azeotrope from EtOH (10 mL×2). This provided 3.167 g active (yield=88%) of product in a purity of 91.5% by HPLC.

Stage 3: Preparation of 5MeO-DMT Fumarate

To a 50 mL 3-neck flask under $N_2$ was charged fumaric acid (1.675 g, 14.430 mmol) and a solution of stage 2 methoxy derivative (3.15 g, 14.430 mmol) in EtOH (37.8 mL). The mixture was then heated to 75° C. for 1 hour, this did not produce a solution as expected, the mixture was further heated to reflux (78° C.) which still failed to provide a solution. The suspension was therefore cooled to 0-5° C., filtered and washed with EtOH (8 mL×2) before being dried at 50° C. overnight. This provided 3.165 g (yield=65%) of material in a purity of 99.9% by HPLC.

α,α-dideutero-5-Methoxydimethyltryptamine

For stage 1 (coupling of 5-methoxyindole-3-acetic acid and dimethylamine), see above.

Stage 2: Preparation of α,α-dideutero-5-Methoxydimethyltryptamine

To a 100 mL 3-neck flask under $N_2$ was charged stage 1 methoxy derivative (3.85 g, 16.586 mmol) and THF (19.25 mL). 2.4 M $LiAlD_4$ in THF (6.22 mL, 14.927 mmol) was then charged dropwise over 30 minutes at <40° C. The reaction mixture was heated to 60° C. for 1 hour where HPLC indicated 0.1% SM (stage 1 methoxy derivative) remained. The reaction mixture was then cooled to ambient temperature and quenched into 25% Rochelle's salts (38.5 mL) dropwise over 30 minutes at <30° C. The resultant suspension was stirred for 1 hour before being allowed to separate. The lower aqueous layer was then removed, and the upper organic layer washed with saturated brine (9.6 mL). The organics were then dried over $MgSO_4$, filtered and concentrated in vacuo before being subjected to an azeotrope from EtOH (10 mL×2). This provided 3.196 g active (yield=88%) of product in a purity of 91.5% by HPLC.

Stage 3: Preparation of α,α-dideutero-5-Methoxydimethyltryptamine Fumarate

To a 50 mL 3-neck flask under $N_2$ was charged fumaric acid (1.675 g, 14.430 mmol) and a solution of stage 2 methoxy derivative (3.15 g, 14.430 mmol) in EtOH (37.8 mL). The mixture was then heated to 75° C. for 1 hour, this did not produce a solution as expected, the mixture was further heated to reflux (78° C.) which still failed to provide a solution. The suspension was therefore cooled to 0-5° C., filtered and washed with EtOH (8 mL×2) before being dried at 50° C. overnight. This provided 3.165 g (yield=65%) of material in a purity of 99.9% by HPLC.

Synthesis of Deuterated Mixtures of DMT Compounds

A modified synthesis at stage 2 using solid $LiAlH_4$/$LiAlD_4$ mixtures was adopted, using 1.8 equivalents of LiAlH$_4$/LiAlD$_4$ versus 0.9 equivalents using the process described above for undeuterated DMT.

Six deuteration reactions were performed.

Representative Synthesis of a Deuterated Mixture (Using 1:1 LiAlH$_4$: LiAlD$_4$) of DMT Compounds To a 250 mL 3-neck flask under N$_2$ was charged LiAlH$_4$ (1.013 g, 26.7 mmol), LiAlD$_4$ (1.120 g, 26.7 mmol) and THF (100 mL). The resultant suspension was stirred for 30 minutes before stage 1 (6 g, 29.666 mmol) was charged portion-wise over 15 minutes at 20-40° C. The reaction mixture was then heated to reflux (66° C.) for 2 hours where HPLC indicated no stage 1 remained. The mixture was cooled to 0° C. and quenched with 25% Rochelle's salts (aq) (120 mL) over 30 minutes at <30° C. The resultant milky suspension was stirred for 1 hour and then allowed to separate. The lower aqueous layer was removed and the upper organic layer washed with saturated brine (30 mL). The organics were then dried over MgSO$_4$, filtered and concentrated in vacuo. This provided 4.3 g of crude material. The crude was then taken up in ethanol (52 mL) and charged with fumaric acid (2.66 g, 22.917 mmol) before heating to 75° C. The resultant solution was allowed to cool to ambient temperature overnight before further cooling to 0-5° C. for 1 hour. The solids were isolated by filtration and washed with cold ethanol (6.5 mL×2). The filtercake was dried at 50° C. overnight to provided 5.7 g (yield=63%) of product in a purity of 99.9% by HPLC and >95% by NMR.

Assessment of Extents of Deuteration

This was achieved by LCMS-SIM (SIM=single ion monitoring), the analysis giving a separate ion count for each mass for the three deuterated N,N-dimethyltryptamine compounds (N,N-dimethyltryptamine (D0), α-deutero-N,N-dimethyltryptamine (D1) and α,α-dideutero-N,N-dimethyltryptamine (D2)) at the retention time for N,N-dimethyltryptamine. The percentage of each component was then calculated from these ion counts.

For example, % D0=[D0/(D0+D1+D2)]×100.

HPLC Parameters

| System: | Agilent 1100/1200 series liquid chromatograph or equivalent |
|---|---|
| Column: | Triart Phenyl; 150 × 4.6 mm, 3.0 μm particle size (Ex: YMC, Part number: TPH12S03-1546PTH) |
| Mobile phase A: | Water:Trifluoroacetic acid (100:0.05%) |
| Mobile phase B: | Acetonitrile:Trifluoroacetic acid (100:0.05%) |

| | Time | % A | % B |
|---|---|---|---|
| Gradient: | 0 | 95 | 5 |
| | 13 | 62 | 38 |
| | 26 | 5 | 95 |
| | 30.5 | 5 | 95 |
| | 31 | 95 | 5 |

| Flow rate: | | 1.0 mL/min | |
|---|---|---|---|
| Stop time: | 31 minutes | Post runtime: | 4 minutes |
| Injection volume: | 5 μL | Wash vial: | N/A |
| Column temperature: | | 30° C. combined | |
| Wavelength: | 200 nm, (4 nm) | Reference: | N/A |

Mass Spectrometry Parameters

| System: | Agilent 6100 series Quadrupole LC-MS or equivalent | | |
|---|---|---|---|
| Drying gas flow: | 12.0 L/min | Drying gas temp.: | 350° C. |
| Nebuliser pressure: | 35 psig | | |
| Fragmentor: | 110 | Gain: | 1.00 |

| Cpd | RT | RRT | Conc | Diluent | Detection | Mass |
|---|---|---|---|---|---|---|
| D0 | 10.64 | 1.00 | 0.30 mg/ml | CH$_3$CN:H$_2$O (50:50) | (+) SIM | 189.10 m/z |
| D1 | 10.64 | 1.00 | 0.30 mg/ml | CH$_3$CN:H$_2$O (50:50) | (+) SIM | 190.10 m/z |
| D2 | 10.64 | 1.00 | 0.30 mg/ml | CH$_3$CN:H$_2$O (50:50) | (+) SIM | 191.10 m/z |

MS-SIM range is the target mass ±0.1 m/z

The data for the six deuterated reactions are tabulated in Table 2 below:

| Mixture No. (LiAlH$_4$:LiAlD$_4$ ratio) | Input (stage 1) | Output stage 3 (yield) | Purity by HPLC | Purity by NMR | Deuteration % | | |
|---|---|---|---|---|---|---|---|
| | | | | | D$_0$ | D$_1$ | D$_2$ |
| 1 (SPL026) (0:1) | 5 g | 5.3 g (65%) | 99.7% | >95% | 0.7% | 2.7% | 96.6% |
| 2 (1:1) | 6 g | 5.699 g (63%) | 99.9% | >95% | 30.0% | 48.3% | 21.7% |
| 3 (1:2) | 5 g | 4.206 g (52%) | 99.9% | >95% | 16.5% | 46.8% | 36.8% |
| 4 (1:3) | 5 g | 5.558 g (68%) | 99.8% | >95% | 9.3% | 41.5% | 49.2% |
| 5 (2:1) | 5 g | 4.218 g (52%) | 99.9% | >95% | 47.5% | 41.3% | 11.2% |
| 6 (3:1) | 5 g | 5.0 g (62%) | 99.4% | >95% | 57.5% | 35.3% | 7.4% |

In Vitro Intrinsic Clearance of DMT (SPL026) and 6 Deuterated Compound Blends

In vitro determination of intrinsic clearance is a valuable model for predicting in vivo hepatic clearance. The liver is the main organ of drug metabolism in the body, containing both phase I and phase II drug metabolising enzymes, which are present in the intact cell.

Aim

To use human hepatocytes to assess the in vitro intrinsic clearance of deuterated DMT analogue blends relative to DMT.

Description of the Experiment

Human (mixed gender) hepatocytes pooled from 10 donors (0.545 million cells/mL) were used to investigate the in vitro intrinsic clearance of DMT and 6 deuterated analogues.

A concentration of 5 μM was used for all test compounds, as well as sumatriptan, serotonin, benzylamine controls. This concentration was chosen in order to maximise the signal-to-noise ratio, while remaining under the Michaelis constant (Km) for the monoamine oxidase enzyme (MAO). Diltiazem and diclofenac controls were used at a laboratory-validated concentration of 1 μM.

Test compounds were mixed with the hepatocyte suspension within a 96-well plate and incubated for up to 60 minutes at 37° C. The suspension was continuously agitated. At 7 time points, small aliquots were withdrawn, and the test compound/blend concentration therein was measured by LC-MS/MS. The time points measured were 2, 4, 8, 15, 30, 45 and 60 minutes.

The following LC-MS/MS conditions were used for the analysis:
Instrument: Thermo TSQ Quantiva with Thermo Vanquish UPLC system
Column: Luna Omega 2.1×50 mm 2.6 μm
Solvent A: $H_2O$+0.1% formic acid
Solvent B: Acetonitrile+0.1% formic acid
Flow rate: 0.8 ml/min
Injection vol: 1 μl
Column temp: 65° C.
Gradient:

| Time (mins) | % Solvent B |
|---|---|
| 0.00 | 5.0 |
| 0.90 | 75.0 |
| 1.36 | 99.0 |
| 1.36 | 5.0 |
| 1.80 | 5.0 |

MS Parameters:
Positive ion spray voltage: 4000 V
Vaporiser temperature: 450° C.
Ion transfer tube temp: 365° C.
Sheath gas: 54
Aux gas: 17
Sweep gas: 1
Dwell time 8 ms
MRM transitions:
  D0=mass to charge ratio 189.14>58.16.
  D1=mass to charge ratio 190.14>59.17.
  D2=mass to charge ratio 191.14>60.17.

The MRM transitions were determined from a preliminary analysis of DMT samples containing either no deuterium (for D0 transition), or high levels of either D1 or D2 deuteration (for the D1 and D2 transitions respectively).

The resulting concentration-time profile was then used to calculate intrinsic clearance (CLint) and half-life (t½). To do this, the MS peak area or MS peak area/IS response of each analyte is plotted on a natural log scale on the y axis versus time (min) of sampling on the X axis. The slope of this line is the elimination rate constant. This is converted to a half-life by −ln(2)/slope. Intrinsic clearance is calculated from the slope/elimination rate constant and the formula is CLint=(−1000*slope)/cell density in 1E6 cells/ml, to give units of microlitre/min/million cells.

Results

Intrinsic clearance and half-life values were calculated for DMT and the 6 deuterated mixtures described above. These data were weighted dependent on the ratio of D0, D1 and D2 to give an overall intrinsic clearance and half-life value for each compound blend (Table 3).

TABLE 3

In vitro intrinsic clearance and calculated half-life of DMT and 6 deuterated mixtures

| Compound name or Mixture No (per Table 1) | $LiAlH_4$:$LiAlD_4$ input ratio | $D_0$:$D_1$:$D_2$ output ratio | Half-life (min) |
|---|---|---|---|
| DMT (SPL026) | 1:0 | 100:0:0 | 92.39 |
| 1 | 0:1 | 0.7:2.7:96.6 | 178.79 |
| 2 | 1:1 | 30.0:48.3:21.7 | 125.80 |
| 3 | 1:2 | 16.5:46.8:36.8 | 140.43 |
| 4 | 1:3 | 9.3:41.5:49.2 | 116.84 |
| 5 | 2:1 | 47.5:41.3:11.2 | 119.61 |
| 6 | 3:1 | 57.4:35.3:7.4 | 95.04 |

Data were fitted with a linear model using regression analysis, which revealed that deuterium enrichment at the α-carbon of DMT decreases intrinsic clearance linearly with increasing molecular weight (MW), therefore enabling manufacture of DMT drug substances with half-lives which can be accurately predicted in the range identified.

Mixture 1, which contains 96.6% D2-DMT, sees the biggest change, with the intrinsic clearance rate almost halved compared to undeuterated-DMT (FIG. 4), nearly doubling the half-life (FIG. 3). Intermediate blends of deuteration (Mixtures 2 to 5) decreased intrinsic clearance in a manner correlated with molecular weight (FIG. 4).

Conclusion

These data demonstrate that increasing deuterium enrichment at the α-carbon of DMT increases metabolic stability, leading to a decrease in clearance and longer half-life. A linear relationship exists between MW and half-life, in particular when the input reducing agent for production of the deuterium enriched DMT-containing drug substance by methods of the present invention comprise $LiAlH_4$ and $LiAlD_4$ with ratio between 1:2.5 and 2.5:1. The relative half-life of analogous mixtures of protio, mono- and di-deutero compounds of formula I are expected to mirror the trends observed here for mixtures of protio, mono- and di-deutero DMT. It is expected that increasing deuterium enrichment at the α-carbon of compounds of formula I increases metabolic stability, leading to a decrease in clearance and longer half-life.

BEST MODE FOR DMT

Stage 1

| Step No. | Process | Comments |
|---|---|---|
| 1A | Prepare a solution of $K_2CO_3$ (aq) by dissolving $K_2CO_3$ (0.5 g/g of limiting reagent) in water (4.5 mL/g) | Caution exothermic. For use in step 11 |
| 2A | Prepare a solution of brine (aq) by dissolving NaCl (0.625 g/g) in water (1.875 mL/g) | For use in step 25 |
| 1 | Charge 3-Indoleacetic acid (1 g/g, limiting reagent) to vessel. | Off-white solid. Total volume = 1 vol |
| 2 | Charge HOBt (0.926 g/g active, 1.2 eq) | White solid, charge calculation is for active amount of HOBt which typically contains ~20% water. Total volume = 1.92 vol |
| 3 | Charge DCM (9 mL/g) | Total volume = 10.92 vol |
| 4 | Start stirrer and stir the contents of vessel at 20 ± 10° C. | No exotherm observed on 257 g scale. White suspension at this point. Hold point - reaction mixture stable for at least 72 hours. |
| 5 | Important-steps 5-18 should preferably be complete within an 8-hour window, recommend against proceeding if this is not done. Charge EDC•HCl (1.31 g/g, 1.2 eq) portion wise at 20 ± 10° C. over at least 5 minutes | Caution - exothermic addition (15-23° C. on an 257 g scale with an addition rate of 5 minutes and Huber temperature control unit set at 20° C.). The batch will form an amber solution as the addition progresses however, some minimal EDC solids may be present in lumps. Total volume = 12.23 vol |
| 6 | Use DCM (1 mL/g) to rinse any residual EDC•HCl into the vessel | |
| 7 | Stir the contents of the vessel at 20 ± 10° C. for at least 1 hour | Typically a solution at this point however some minimal EDC•HCl solids may be present in lumps. Total volume = 13.23 vol |
| 8 | Charge 2M dimethylamine in THF (4.281 mL/g, 1.5 eq) at 20 ± 10° C. over at least 15 minutes | Caution - exothermic addition (20-30° C. on an 257 g scale with an addition rate of 20 minutes and Huber temperature control unit set at 10° C. Total volume = 16.51 vol |
| 9 | Stir the contents of the vessel at 20 ± 10° C. for at least 1 hour | |
| 10 | IPC 1 | Dilution 1 in 300 MeCN Ensure all RTIDs are ran prior to IPC 1 to minimise stir out time at this point. |
| 11 | Charge the pre-made solution of $K_2CO_3$ (aq) from step 1A at 20 ± 10° C. | No exotherm observed on 257 g scale with addition as one portion. Total volume = 21.51 vol |
| 12 | Stir the contents of the vessel at 20 ± 10° C. for at least 5 minutes | |
| 13 | Stop the stirrer and allow layers to separate | Fast separation on 257 g scale <5 minutes. Upper layer (aqueous) - colourless/pale yellow Lower layer (DCM) - Amber |
| 14 | Remove the lower organic layer and retain the upper aqueous layer in the vessel | Store lower organic layer for use in step 24 |
| 15 | Charge DCM (2.5 mL/g) to the vessel at 20 ± 10° C. | Total volume = 7.5 vol |
| 16 | Stir the contents of the vessel at 20 ± 10° C. for at least 5 minutes | |
| 17 | Stop the stirrer and allow layers to separate | Fast separation on 257 g scale <5 minutes. Upper layer (aqueous) - colourless/pale yellow Lower layer (DCM) - Amber |
| 18 | Remove the lower organic layer and retain the upper aqueous layer in the vessel | Store lower organic layer for use in step 24 |
| 19 | Charge DCM (2.5 mL/g) to the vessel at 20 ± 10° C. | Total volume = 7.5 vol |
| 20 | Stir the contents of the vessel at 20 ± 10° C. for at least 5 minutes | |
| 21 | Stop the stirrer and allow layers to separate | Fast separation on 257 g scale <5 minutes. Upper layer (aqueous) - colourless/pale yellow Lower layer (DCM) - Amber |
| 22 | Remove the lower organic layer | Store lower organic layer for use in step 24. |
| 23 | Remove the upper aqueous layer | Analyse by HPLC and dispose of as per COSHH. |
| 24 | Charge the DCM extracts from steps 14, 18 and 22 back to the vessel | |
| 25 | Charge the premade brine solution from step 2A at 20 ± 10° C. | Total volume = 22.5 vol |
| 26 | Stir the contents of the vessel at 20 ± 10° C. for at least 5 minutes | |
| 27 | Stop the stirrer and allow the layers to separate | Fast separation on 257 g scale <5 minutes. Upper layer (aqueous) - colourless/pale yellow Lower layer (DCM) - Amber |
| 28 | Remove the lower organic layer | Hold point - organic layer stable as a solution for at least 72 hours |
| 29 | Remove the upper aqueous layer | Analyse by HPLC and dispose of as per COSHH. |
| 30 | Dry the lower DCM layer from step 28 over $MgSO_4$ | |
| 31 | Filter the batch | |
| 32 | Charge DCM (to be judged by chemist) to the vessel and use this to wash any residual solids onto the filter cake | Typically used 1-2 volumes during development. |
| 33 | Concentrate the filtrate in vacuo $T_{max}$ = 50° C. | |
| 34 | Expected crude mass ~1.18 g/g-1.21 g/g | Crude typically an off-white solid, may require pre-grinding prior to use in step 35. |
| 35 | Charge the crude material from step 33 back to a clean vessel | |
| 36 | Charge TBME (10 mL/g) | No exotherm observed on 257 g scale |
| 37 | Stir the contents of the vessel at 50 ± 5° C. for at least 2 hours | This should give a homogenous suspension, if there are still visible lumps after the 2 hours stir out, continue to stir until a homogenous suspension is achieved. Hold point - stable for at least 72 hours |
| 38 | Cool the contents of the vessel to 20 ± 5° C. | |

-continued

| Step No. | Process | Comments |
| --- | --- | --- |
| 39 | Filter the batch | Pull dry before proceeding to the next step |
| 40 | Charge TBME (5 mL/g) to the vessel and use this to rinse any residual solids onto the filter cake | Pull each wash dry before proceeding to the next wash |
| 41 | Discharge the filtercake to the oven | |
| 42 | Dry the filtercake at 50° C. for at least 16 hours | |
| 43 | Expected batch weight ~1.036 g/g, 90% yield | |

Vessel Cleaning

| Step | Process | Information |
| --- | --- | --- |
| 32 | Decontaminate with DCM, then carry out a water/methanol cleanout | — |
| 40 | Decontaminate with DCM, then carry out a water/methanol cleanout | — |

Stress Tests

| Step No | Process | Information |
| --- | --- | --- |
| 4 | Stirred at RT for 72 hours | Stable |
| 7 | Complete reaction mixture stirred for additional 18 hrs | Unstable - do not stir overnight. |
| 8 | Complete reaction mixture stirred for additional 18 hrs | Unstable - do not stir overnight. |
| 18 | DCM/$K_2CO_3$ mixture held overnight | Stable |
| 28 | Held for 72 hours post $K_2CO_3$ and brine washes | Stable |
| 33 | Concentrated (~2-3 vol) reaction mixture held at 45° C. for 18 hrs | Stable |
| 37 | Slurry held for additional 18 hrs and 72 hrs after 2 hrs stir out at 50° C. | Stable |
| 42 | Batch dried at 50° C. for 72 hours | Stable |

List of Solvents and Reagents

| Solvent/Reagent | Specification |
| --- | --- |
| 3-Indole acetic acid | Standard - Carbosynth, Cat number: FI09866, purity: 98% |
| DCM | Standard |
| EDC | Standard Fluorochem, Cat number: 0241810, purity: 99% |
| HOBt | Standard - Fluorochem, Cat number: M02875, purity: 99% |
| 2M Dimethylamine in THF | Do not sample |
| $K_2CO_3$ | Standard - Brenntag 325 mesh used in dev |
| Water | Do not sample - purified |
| NaCl | Standard |

Processing Analysis

Stage 1 in Process Analysis 1

| Test | Specification limit |
| --- | --- |
| HPLC (N,N-DMT method, 220 nm) - 1 in 300 dilution in MeCN | Stage 1 intermediate 1 - (relative retention time (RRT) 1.377) not more than (NMT) 0.15%<br>Stage 1 intermediate 2 - (RRT 1.488) NMT 0.15%<br>3-indoleacetic acid - (RRT 0.966) NMT 2.0%<br>Stage 1 - (RRT 1.0, retention time (RT) - 14.029 min) not less than (NLT) 97.0%<br>HOBt - (RRT 0.458) do not integrate |

Stage 1B Intermediate Analysis—QA Check Required

| Test | Specification limit |
| --- | --- |
| Appearance | Report result |
| Identity by $^1$H-NMR (CDCl$_3$) | Spectrum conforms to reference |
| HPLC (N,N-DMT method, 220 nm) | Stage 1 intermediate 1 - (RRT 1.377) report result - typically ND<br>Stage 1 intermediate 2 - (RRT 1.488) report result - typically ND<br>3-indoleacetic acid - (RRT 0.966) report result - typically less than (LT) 0.2%<br>Stage 1 - (RRT 1.0, RT - 14.029 min) report result - typically NLT 97%<br>HOBt - (RRT 0.458) report results - typically NMT 2% |

Stage 2

| Step No. | Process | Comments |
| --- | --- | --- |
| 1 | Charge stage 1 (1 g/g limiting reagent) to vessel 1 | Off-white solid<br>Total volume = 1 vol |
| 2 | IPC 1 | THF water content by Karl Fisher titration (KF) NMT 200 ppm |
| 3 | Charge THF (5 mL/g) to vessel 1 | Total volume = 6 vol |
| 4 | Start stirrer and stir the contents of vessel at 20 ± 10° C. | Off-white suspension at this point |
| 5 | Charge 2M LiAlH$_4$ in THF (2.225 mL/g, 0.9 eq) to vessel 1 dropwise over at least 30 minutes at 30 ± 35° C. | Caution - highly exothermic addition (18-58° C. on a 272.5 g scale with an addition rate of 35 minutes and Huber temperature control unit set at 20° C.).<br>2.4M LiAlH$_4$ (1.854 g/g) diluted with THF (0.371 mL/g) to give 2M LiAlH$_4$ during development.<br>Batch typically forms an amber solution ~⅓-½ of the way through addition<br>Total volume = 8.225 vol |
| 6 | Heat the contents of vessel 1 to 60 ± 5° C. | |
| 7 | Stir the contents of vessel 1 at 60 ± 5° C. for at least 2 hours | Unstable - do not stir overnight at temperature |
| 8 | IPC 2 | |
| 9 | Cool the contents of vessel 1 to 20 ± 10° C. | Hold point - stable for 18 hours, however, increase in impurity profile with 72 hours stir out<br>Recommend - do not to hold at this step for longer than necessary. |
| 10 | Charge Rochelle's salts (2.5 g/g) to vessel 2 | Total volume = 2.5 vol |

-continued

| Step No. | Process | Comments |
|---|---|---|
| 11 | Charge water (7.5 mL/g) to vessel 2 at 20 ± 10° C. | Total volume = 10 vol |
| 12 | Start the stirrer and stir the contents of vessel 2 at 20 ± 10° C. for at least 15 minutes to achieve a solution | Typically, a solution at this point however, some minimal Rochelle's salts may still be present. |
| 13 | Charge the contents of vessel 1 to vessel 2 at 20 ± 10° C. over at least 30 minutes | Caution - highly exothermic addition (18-28° C. on a 272.5 g scale with an addition rate of 30 minutes and Huber temperature control unit set at 0° C.). A milky white suspension will form as the addition progresses, ensure adequate stirring to avoid adhering to the vessel walls. Total volume = 18.225 vol |
| 14 | Charge THF (0.5 mL/g) to vessel 1 at 20 ± 10° C. | This is a line rinse, not carried out during development. However, may be required on large scale (50 L) processing. Total volume = 18.725 vol |
| 15 | Stir the contents of the vessel 1 20 ± 10° C. for at least 5 minutes | |
| 16 | Charge the contents of vessel 1 to vessel 2 at 20 ± 10° C. over at least 15 minutes | |
| 17 | Stir the contents of vessel 2 at 20 ± 10° C. for at least 1 hour | Hold point - quenched reaction mixture stable for at least 72 hours |
| 18 | Stop the stirrer and allow the layers to separate for at least 30 minutes. | Fast separation <5 minutes on 272.5 g scale however, 30-minute separation time will aid removal of the lower layer at step 19. Upper layer (organic) - clear amber solution Lower layer (aqueous) - milky white suspension which will settle to give a pale-yellow solution with solids in the bottom. |
| 19 | Remove the lower aqueous layer and retain the upper organic layer in the vessel | Analyse by HPLC and dispose of as per COSHH. |
| 20 | Prepare a solution of brine (aq) by dissolving NaCl (0.625 g/g) in water (1.875 mL/g) | For use in step 21 |
| 21 | Charge the premade solution from step 20 to vessel 2 at 20 ± 10° C. | Total volume = 10.725 vol |
| 22 | Stir the contents of vessel 2 at 20 ± 10° C. for at least 5 minutes | |
| 23 | Stop the stirrer and allow the layers to separate | Fast separation <5 minutes on 272.5 g scale Upper layer (organic) - dark amber solution Lower layer (aqueous) - pale yellow |
| 24 | Remove the lower aqueous layer | Analyse by HPLC and dispose of as per COSHH. |
| 25 | Remove the upper organic layer | Store for use in step 26 |
| 26 | Dry the upper organic layer from step 25 over MgSO$_4$ | |
| 27 | Filter the batch | |
| 28 | Charge THF (to be judged by chemist) to the vessel and use this to wash any residual solids onto the filter cake | Typically used 1-2 volumes during development. |
| 29 | Concentrate the filtrate in vacuo $T_{max}$ = 50° C. | Hold point - Stable for at least 72 hours |
| 30 | Charge EtOH (2 mL/g) | |
| 31 | Concentrate in vacuo $T_{max}$ = 50° C. | |
| 32 | IPC 3 | If IPC is not met repeat steps 30-31 |
| 33 | Expected batch weight 0.792 g/g, 91% yield | Typically, an amber oil which may crystalize on standing. Typically contains 3-5% EtOH at this point however, this may vary depending on scale. |

Vessel Cleaning

| Step | Process | Information |
|---|---|---|
| 33 | Decontaminate with THF then carry out an acetone/water clean out | — |

Stress Tests

| Step No | Process | Information |
|---|---|---|
| 7 | Complete rxn held at 60° C. for 18 h and 72 h | Unstable - do not stir overnight |
| 7 | Complete rxn cooled to RT and held for 18 h and 72 h | Stable for 18 hours, increase in impurity profile with a 72 hour stir out |
| 17 | Held at RT for 18 h and 72 h | Stable |
| 18 | Stirrer stopped and layers held at 18 h and 72 h | Stable |
| 29 | Mixture held at 50° C. for 18 hours and 72 hours | Stable |

List of Solvents and Reagents

| Solvent/Reagent | Specification |
|---|---|
| THF | Standard - NMT 200 ppm water by KF |
| 2.4M LiAlH$_4$ | Do not sample - Aldrich, Cat number: 1002778187 |
| Rochelle's salts | Standard - Alfa Aesar, Cat number: A10163, purity 99% |
| NaCl | Standard |
| Water | Do not sample - purified |
| MgSO$_4$ | Standard |

Processing Analysis
Stage 2 in Process Analysis 1

| Test | Specification limit |
|---|---|
| Water content of THF by KF | NMT 200 ppm |

Stage 2 in Process Analysis 2

| Test | Specification limit |
|---|---|
| HPLC (N,N-DMT method, 220 nm) - 1 in 300 dilution in MeOH | Stage 1 (RRT 1.305) - NMT 0.15% Stage 2 (RRT 1.0 10.7 min) - Typically 94% Stage 2 impurity 1 (RRT 1.269) Typically 2.7% Stage 2 impurity 2 (RRT 1.416) Typically 1.9% HOBt - (RRT 0.603) do not integrate |

Stage 2 in Process Analysis 3

| Test | Specification limit |
| --- | --- |
| THF/EtOH content by NMR (CDCl$_3$) | THF - NMT 720 ppm<br>EtOH - Report result |

Stage 2B Intermediate Analysis—QA Check Required

| Test | Specification limit |
| --- | --- |
| Appearance | Report result |
| Identity by $^1$H-NMR (CDCl$_3$) | Spectrum conforms to reference |
| HPLC (N,N-DMT method, 220 nm) - 1 in 300 dilution in MeOH | Stage 1 (RRT 1.305) report result - typically ND<br>Stage 2 (RRT 1.0 10.700 min) report result - typically 95.0%<br>Stage 2 impurity 1 (RRT 1.269) report result - typically 3.2%<br>Stage 2 impurity 2 (RRT 1.416) report result - typically ND<br>HOBt - (RRT 0.603) report result - typically 0.1% |

Stage 3

| Step No. | Process | Comments |
| --- | --- | --- |
| 1 | Dissolve stage 2 (1 g/g Active, limiting reagent) in EtOH (10 mL/g) at 20 ± 20° C. | Stage 2 active content based on NMR purity. Typically 3.5% EtOH - (100-3.5 = 96.5% active) Stage 2B is typically an oil however, it may crystalize on standing. This was done using a rotary evaporator on a 248 g scale, dissolved in ~15 minutes at 40° C. |
| 2 | Charge Fumaric acid (0.616 g/g, 1 eq) to vessel 1 | Fumaric acid is a white crystalline solid |
| 3 | Charge the premade solution from step 1 into vessel 1 at 20 ± 10° C. | |
| 4 | Use EtOH (2 mL/g) to rinse any residual stage 2B and fumaric acid into vessel 1 | |
| 4 | Start the stirrer and stir at 20 ± 10° C. | Thin suspension of fumaric acid at this point |
| 5 | Heat the contents of vessel 1 to 75 ± 3° C. | A brown solution is typically formed at temperatures above 65° C. Unstable - do not stir overnight |
| 6 | Preheat vessel 2 to 75 ± 3° C. | |
| 7 | Polish filter the contents of vessel 1 into vessel 2 at 75 ± 3° C. | Vacuum transfer used in development |
| 8 | Cool the contents of vessel 2 to 70 ± 3° C. | The mixture should still be a solution at this point. |
| 9 | Charge N,N-DMT fumarate (Pattern A) seed (0.001 g/g) to vessel 2 | A small amount of seed should be visible at this step. |
| 10 | Stir the contents of vessel 2 at 70 ± 3° C. for at least 30 minutes | A thin suspension will typically develop during this step. Unstable - do not stir overnight |
| 11 | Cool the contents of vessel 2 to 0 ± 5° C. at a rate of 5° C. per hour | This should take ~14 hours. Suspension typically develops as cooling progresses |
| 12 | Stir the contents of vessel 2 at 0 ± 5° C. for at least 1 hour | |
| 13 | Filter the contents of vessel 2 | |
| 14 | Charge EtOH (2 mL/g) to vessel 2 at 20 ± 10° C. | EtOH must be polish filtered |
| 15 | Cool the contents of vessel 2 to 0 ± 5° C. | |
| 16 | Use the contents of vessel 2 to wash the filter cake from step 13 | Ensure filter cake is pulled dry and smoothed over before applying the washes. |
| 17 | Charge EtOH (2 mL/g) to vessel 2 at 20 ± 10° C. | EtOH must be polish filtered |
| 18 | Cool the contents of vessel 2 to 0 ± 5° C. | |
| 19 | Use the contents of vessel 2 to wash the filter cake from step 13 | Ensure filter cake is pulled dry and smoothed over before applying the washes. |
| 20 | Pull the filter cake dry for at least 30 minutes | |
| 21 | Discharge the filter cake to the oven | Typical wet weight 1.3-1.4 g/g |
| 22 | Dry at 50° C. for at least 16 hours | |
| 23 | IPC 1 | If IPC is not met, continue to dry at 50° C. and sample at appropriate intervals. If IPC is still not met after drying at 50° C. for at least 72 hours, seek technical advice. |
| 24 | Expected batch weight 1.26 g/g, 78% yield | |
| 25 | Submit for final product analysis as per specification | |

Vessel Cleaning

| Step | Process | Information |
| --- | --- | --- |
| 8 | Water then acetone clean out of vessel 1 | API highly soluble in water |
| 25 | Water then acetone clean out of vessel 2 | API highly soluble in water |

Stress Tests

| Step No | Process | Information |
| --- | --- | --- |
| 1 | Stage 2B held as a solution in EtOH for 1 week | Stable |
| 7 | Held at 75 ± 3° C. for 18 and 72 hours | Unstable - do not stir overnight |
| 22 | Dried at 50° C. for 18 and 72 hours | Stable |
| 22 | Wetcake held in a sealed container at 50° C. for 18 and 72 hours | Stable |

List of Solvents and Reagents

| Solvent/Reagent | Specification |
| --- | --- |
| Fumaric acid | Standard - Cat number: A10976, purity: 99%, Supplier: Alfa Aesar |
| EtOH | Standard |

Stage 3 in Process Analysis 1—QA Check Required

| Test | Specification limit |
|---|---|
| EtOH content by $^1$H-NMR (DMSO) | NMT 0.5% - (typically 0.05%) |

The invention claimed is:

1. A method of treating a psychiatric or neurological disorder in a patient in need thereof, comprising administering to the patient in need thereof a compound of formula I, or a pharmaceutically acceptable salt thereof:

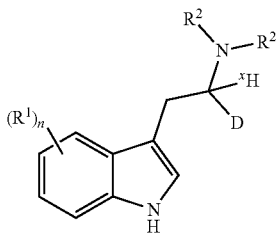

I wherein $^x$H is protium or deuterium,
n is selected from 1, 2, 3 or 4,
$R^1$ is independently selected from —$R^3$, —$OR^3$, —$O(CO)R^3$, —F, —Cl, —Br or —I, and
$R^2$ and $R^3$ are independently selected from $C_1$-$C_4$alkyl.

2. The method of claim 1, wherein the psychiatric or neurological disorder is selected from (i) an obsessive compulsive disorder, (ii) a depressive disorder, (iii) a schizophrenia disorder, (iv) a schizotypal disorder, (v) an anxiety disorder, (vi) substance abuse, and (vii) an avolition disorder.

3. The method of claim 1, wherein the disorder is major depressive disorder.

4. The method of claim 1, wherein the disorder is treatment resistant depression.

5. The method of claim 1, wherein said administering is accomplished by oral administration.

6. The method of claim 1, wherein $R^2$ is methyl, or wherein $R^1$ is independently selected from $OR^3$ and —$O(CO)R^3$, or wherein $R^3$ is methyl, or wherein $R^1$ is methoxy, or wherein n is 1, or wherein $R^1$ is at the 4- or 5-position, or wherein $^x$H is deuterium.

7. The method of claim 1, wherein n is 1 and $R^1$ is 5-methoxy.

8. The method of claim 1, wherein the compound of formula I has a purity of between 99% and 100% by HPLC.

9. The method of claim 1, wherein the compound of formula I is in the form of a pharmaceutically acceptable salt.

10. The method of claim 9, wherein the pharmaceutically acceptable salt is a fumarate salt.

11. A method of treating a psychiatric or neurological disorder in a patient in need thereof, comprising administering to the patient in need thereof a pharmaceutical composition comprising:
a) a compound of formula I in the form of a pharmaceutically acceptable salt,

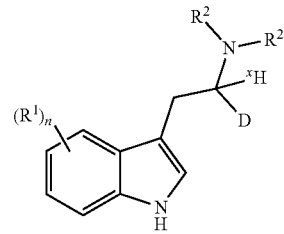

I wherein $^x$H is protium or deuterium,
n is selected from 1, 2, 3 or 4,
$R^1$ is independently selected from —$R^3$, —$OR^3$, —$O(CO)R^3$, —F, —Cl, —Br or —I, and
$R^2$ and $R^3$ are independently selected from $C_1$-$C_4$alkyl; and
b) a pharmaceutically acceptably excipient.

12. The method of claim 11, wherein the psychiatric or neurological disorder is selected from (i) an obsessive compulsive disorder, (ii) a depressive disorder, (iii) a schizophrenia disorder, (iv) a schizotypal disorder, (v) an anxiety disorder, (vi) substance abuse, and (vii) an avolition disorder.

13. The method of claim 11, wherein the disorder is major depressive disorder.

14. The method of claim 11, wherein the disorder is treatment resistant depression.

15. The method of claim 11, wherein said administering is accomplished by oral administration.

16. A method of treating a psychiatric or neurological disorder in a patient in need thereof, comprising administering to the patient in need thereof a composition comprising at least a first and a second compound, or pharmaceutically acceptable salts thereof, wherein the first compound is selected from a compound of formula I as defined in claim 1, and the second compound is an undeuterated analogue of the first compound.

17. The method of claim 16, wherein the psychiatric or neurological disorder is selected from (i) an obsessive compulsive disorder, (ii) a depressive disorder, (iii) a schizophrenia disorder, (iv) a schizotypal disorder, (v) an anxiety disorder, (vi) substance abuse, and (vii) an avolition disorder.

18. The method of claim 16, wherein the disorder is major depressive disorder.

19. The method of claim 16, wherein the disorder is treatment resistant depression.

20. The method of claim 16, wherein said administering is accomplished by oral administration.

* * * * *